(12) United States Patent
Goldberg et al.

(10) Patent No.: US 6,387,379 B1
(45) Date of Patent: May 14, 2002

(54) BIOFUNCTIONAL SURFACE MODIFIED OCULAR IMPLANTS, SURGICAL INSTRUMENTS, MEDICAL DEVICES, PROSTHESES, CONTACT LENSES AND THE LIKE

(75) Inventors: Eugene P. Goldberg, Gainesville, FL (US); Ali Yahiaoui, Roswell, GA (US); Khalid Mentak, Goleta (MA); Theresa Rivero Erickson, Salt Lake City, UT (US); James Seeger, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 08/202,647

(22) Filed: Feb. 28, 1994

Related U.S. Application Data

(63) Continuation-in-part of application No. 07/859,016, filed on Mar. 30, 1992, now Pat. No. 5,290,548, which is a continuation-in-part of application No. 07/592,483, filed on Oct. 5, 1990, now Pat. No. 5,130,160, which is a continuation-in-part of application No. 07/592,482, filed on Oct. 5, 1990, now Pat. No. 5,100,689, which is a continuation-in-part of application No. 07/592,478, filed on Oct. 5, 1990, now Pat. No. 5,108,776, which is a continuation-in-part of application No. 07/555,377, filed on Jul. 19, 1990, now Pat. No. 5,080,893, which is a continuation-in-part of application No. 07/304,479, filed on Feb. 1, 1989, now Pat. No. 4,961,954, which is a continuation-in-part of application No. 07/037,153, filed on Apr. 10, 1987, now Pat. No. 4,806,382, application No. 08/202,647, which is a continuation-in-part of application No. 08/003,682, filed on Jan. 13, 1993, now Pat. No. 5,376,400.

(51) Int. Cl.$^7$ .......................... A61L 27/16; A61L 27/34; A61L 27/54

(52) U.S. Cl. ...................... 424/400; 427/492; 427/495; 427/496; 427/498; 427/507; 427/535; 427/536; 427/539; 427/491; 427/2.1; 427/2.12; 606/151; 606/159; 604/93; 623/8; 523/106

(58) Field of Search .............................. 424/78.18, 400; 427/492, 495, 496, 498, 507, 535–36, 539, 491, 2.1, 2.12; 606/151, 159; 604/93; 623/8; 523/6

(56) References Cited

U.S. PATENT DOCUMENTS 3,566,874 A * 3/1971 Shepherd et al. ........... 424/422

(List continued on next page.)

OTHER PUBLICATIONS

Trans. Am. Acad. Ophthalmol. Otolaryngol., vol. 83, Katz et al, OP–204–OP–212 (1977).

(List continued on next page.)

Primary Examiner—Edward J. Webman
(74) Attorney, Agent, or Firm—Miles & Stockbridge; Dennis P. Clarke

(57) ABSTRACT

A method for modifying the surface of a material adapted for contact with tissue of a human or non-human animal to impart biofunctional, bioactive or biomimetic properties to the surface comprising:

(a) exposing the surface to a solution comprising (1) an ethylenically unsaturated monomer or mixture thereof capable, via the ethylenic unsaturation, of gamma irradiation or electron beam induced polymerization, and (2) at least one biofunctional agent; and (b) irradiating the surface with gamma or electron beam irradiation in the presence of the solution to thereby form on the surface a graft polymerized coating, the coating having physically entrapped therein or chemically bonded thereto molecules of the at least one biofunctional agent which imparts biofunctional or biomimetic properties to the surface;

wherein the gamma or electron beam irradiation induced polymerization is conducted under one of the following conditions:

A.
(i) monomer concentration in the solution in the range of from about 0.1% to about 50%, by weight;
(ii) total gamma or electron beam dose in the range of from about 0.001 to less than about 0.50 Mrad; and
(iii) gamma dose rate in the range of from about 10 to about 2,500 rads/min., or electron beam dose rate in the range of from about 10 to about $10^8$ rads/min.;

B.
(i) hydrophilic monomer(s) graft under conditions which may include monomer pre-soak or plasma gamma surface modification (especially for metal or glass substrates in latter case); and
(ii) graft polymerization of monomer(s) with bioactive/biofunctional molecules using (i) as substrate;

C.
(i) Hydrograft™ as in A or B above followed by dehydration and adsorption of bioactive/biofunctional molecules into the hydrophilic polymer graft;

wherein the biological properties of the biofunctional agent are substantially maintained.

51 Claims, 8 Drawing Sheets

U.S. PATENT DOCUMENTS

| | | | |
|---|---|---|---|
| 4,554,155 A | * 11/1985 | Allan et al. | 424/419 |
| 4,806,382 A | 2/1989 | Goldberg et al. | 427/2 |
| 4,961,954 A | 10/1990 | Goldberg et al. | 427/2 |
| 5,080,893 A | 1/1992 | Goldberg et al. | 514/57 |
| 5,094,876 A | 3/1992 | Goldberg et al. | 427/2 |
| 5,100,689 A | 3/1992 | Goldberg et al. | 427/2 |
| 5,108,776 A | 4/1992 | Goldberg et al. | 427/2 |
| 5,130,160 A | 7/1992 | Goldberg et al. | 427/2 |
| 5,290,548 A | 3/1994 | Goldberg et al. | 424/78.18 |
| 5,376,400 A | 12/1994 | Goldberg et al. | 427/2.24 |

OTHER PUBLICATIONS

Chemical Abstracts, vol. 92:203547f, Knight et al (1980).

Acta: XXIV, International Congress of Ophthalmology, Yalon et al, ed. Paul Henkind (1983).

* cited by examiner

BIOFUNCTIONAL SURFACE MODIFIED OCULAR IMPLANTS, SURGICAL INSTRUMENTS, MEDICAL DEVICES, PROSTHESES, CONTACT LENSES AND THE LIKE

RELATED APPLICATIONS

This is a continuation-in-part of application Ser. No. 07/859,016 filed Mar. 30, 1992, now U.S. Pat. No. 5,290, 548, which is a continuation-in-part of application Ser. No. 07/555,377 filed Jul. 19, 1990 (U.S. Pat. No. 5,080,893); Ser. No. 07/592,478 filed Oct. 5, 1990 (U.S. Pat. No. 5,108,776); Ser. No. 07/592,482 filed Oct. 5, 1990 (U.S. Pat. No. 5,100,689); and Ser. No. 07/592,483 filed Oct. 5, 1990 (U.S. Pat. No. 5,130,160), which are continuations-in-part of application Ser. No. 07/304,479 filed Feb. 1, 1989 (U.S. Pat. No. 4,961,954), which is a continuation-in-part of application Ser. No. 07/037,153 filed Apr. 10, 1987 (U.S. Pat. No. 4,806,382). This is also a continuation-in-part of application Ser. No. 08/003,682 filed Jan. 13, 1993 now U.S. Pat. No. 5,376,400.

BACKGROUND OF THE INVENTION

1. Field of the Invention

The present invention relates to materials or articles, the surfaces of which are adapted for contact with human or non-human animal tissue, and methods for enhancing the biofunctional properties of the tissue contacting surfaces thereof.

2. Discussion of the Prior Art

At the present time, surgical instruments, various medical devices, catheters, prosthetic implants, endoscopic and minimal invasive surgical devices, contact lenses and the like which are intended for contact with blood or with sensitive tissue surfaces are constructed of materials having the necessary physical properties to enable their use for the intended application; however, they suffer from the disadvantage that due to the generally hydrophobic nature of the blood or tissue contacting surfaces thereof, they exhibit undesired thrombogenic properties and, as noted in the following discussion for ocular implants, significant damage may occur to various fragile or sensitive tissues (i.e., vascular and corneal endothelium, tracheal and ureteral serosal tissues, etc.) by adhesion and manipulation or movement on contact with these instruments.

In U.S. Pat. No. 4,961,954, there are described improved methods for producing hydrophilic, gamma irradiation induced polymerized and chemically grafted coatings on such instruments, devices and the like so constructed of a variety of polymeric materials.

The invention described in U.S. Pat. No. 4,961,954 is predicated on the discovery of certain process conditions and parameters that produce thin, hydrophilic, gamma or electron beam irradiation polymerized and chemically grafted coatings of N-vinylpyrrolidone (NVP [PVP]), copolymerized NVP and 2-hydroxyethylmethacrylate (HEMA) [P(NVP-HEMA)] or HEMA [PHEMA] on the surfaces of articles adapted for contact with living tissue of a human or non-human animal, e.g., surgical instruments, medical devices, prosthetic implants, contact lenses and the like constructed of a wide variety of plastic materials. For purposes of the following description of the present invention, the term "tissue" is intended to include blood as well as solid tissue surfaces.

The surface modifications or chemically grafted coatings of the present invention increase the hydrophilicity of the article surfaces and minimize adhesion and abrasive interactions between the surface and sensitive tissues and cells such as fragile ocular tissues (i.e., iris and corneal endothelium), blood cells, vascular endothelium, peritoneum, pericardium and the like, thereby minimizing tissue damage and complications occasioned by contact between the article and such tissues. The coatings produced are thin and reproducibly uniform. Moreover, they are chemically bound to the surface of the article and, therefore, are far more durable and less subject to removal, degradation or deterioration during or following utilization of the articles than the coatings produced by prior art methods.

Studies have shown that the surgical implantation of ocular implants such as intraocular lenses (IOLs) and the like can result in the loss of significant corneal endothelial tissue unless great care is taken to ensure a lack of contact between the device and the endothelium. Most ocular implants are constructed of hydrophobic polymethylmethacrylate (PMMA) polymers because of their superior optical qualities, resistance to biodegradation, and the like. It has been found, however, that PMMA surfaces adhere to endothelial cells upon even casual contact and that separation of the surface therefrom results in a tearing away of the endothelial tissue adhered to the polymer surface. Similar adhesive interactions with other ocular tissues, i.e., the iris, can also cause adverse tissue damage. Other hydrophobic polymers which are used or have been proposed for use in ocular implants (i.e., polypropylene, polyvinylidene fluoride, polycarbonate, polysiloxane) also can adhere to ocular tissue and thereby promote tissue damage.

It is well documented in the prior art that a significant disadvantage inherent in PMMA IOLs resides in the fact that any brief, non-traumatic contact between corneal endothelium and PMMA surfaces results in extensive damage to the endothelium. See Bourne et al, Am. J. Ophthalmol., Vol. 81, pp. 482–485 (1976); Forster et al, Trans. Am. Acad. Ophthalmol. Otolaryngol., Vol. 83, OP-195-OP-203 (1977); Katz et al, Trans. Am. Acad. Ophthalmol. Otolaryngol., Vol. 83, OP-204-OP-212 (1977); Kaufman et al, Science, Vol. 198, pp. 525–527 (1977) and Sugar et al, Arch. Ophthalmol., Vol. 96, pp. 449–450 (1978) for a discussion of the problems associated with implant surface/endothelium contact.

Since it is extremely difficult to avoid any contact between implant surfaces and endothelium during surgical procedures and especially to other sensitive ocular tissues during implant life, i.e., the iris, ciliary sulcus and the like, efforts have been undertaken to modify the PMMA ocular implant surfaces to reduce the tendency thereof to adhere to and damage corneal endothelium.

Ocular implant surfaces have been coated with various hydrophilic polymer solutions or temporary soluble coatings such as methylcellulose, polyvinylpyrrolidone (Katz et al and Knight et al [Chem. Abs., Vol. 92:203547f (1980)]), etc., to reduce the degree of adhesion between the implant surfaces and tissue cells. While offering some temporary protection, these methods have not proven entirely satisfactory since such coatings complicate surgery, do not adhere adequately to the implant surfaces, become dislodged or deteriorate after implantation, dissolve away rapidly during or soon after surgery or may produce adverse post-operative complications. Moreover, it is difficult to control the thicknesses and uniformity of such coatings.

Yalon et al [Acta: XXIV, International Congress of Ophthalmology, ed. Paul Henkind (1983)] and Knight et al, supra, have reported attempts to produce protective coatings on PMMA implant surfaces by gamma irradiation induced polymerization of vinylpyrrolidone thereon. Their efforts were not altogether successful, however, since their methods also presented problems in controlling the optical and tissue protective qualities of the coatings. Process conditions and parameters (i.e., monomer concentration solvent, dose and dose rate) were not specified. The resulting coatings were of poor quality and non-uniform mechanical stability.

In U.S. Pat. No. 4,806,382, issued Feb. 21, 1989, there are described improved methods for producing hydrophilic, gamma irradiation induced polymerized and chemically grafted coatings on ocular implants constructed of a variety of polymeric materials, which methods overcome the above-noted difficulties and disadvantages.

The invention described in that patent is predicated on the discovery of certain process conditions and parameters that produce thin hydrophilic gamma irradiation induced polymerized and chemically grafted coatings of N-vinylpyrrolidone (NVP) [PVP], copolymerized NVP and 2-hydroxyethylmethacrylate (HEMA) [P(NVP-HEMA)], or HEMA [PHEMA] and their copolymers, particularly with ionic comonomers on the surfaces of ocular implants constructed of materials including polymethylmethacrylate (PMMA) and of other process conditions and parameters which produce thin gamma irradiation induced graft PVP, P(NVP-HEMA), PHEMA or copolymer coatings on the surfaces of ocular implant articles constructed of materials including polypropylene (PP), polyvinylidene fluoride (PVDF), polycarbonate (PC) and polysiloxane or silicone (PDMSO). The coatings increase the hydrophilicity of the implant surface and minimize adhesion between the surface and sensitive ocular tissues such as corneal endothelium or iris, thereby minimizing tissue damage and post-operative complications occasioned by contact between the implant surface and ocular tissue. The coatings produced by the improved method of the invention described in U.S. Pat. No. 4,806,382 are thin and uniform. Moreover, they are chemically bound to the surface of the ocular implant and, therefore, far more durable and less subject to removal, degradation or deterioration during or following surgery than the coatings produced by prior art methods.

The improved gamma irradiation induced graft polymerization of NVP, HEMA or mixtures of NVP and HEMA on ocular implant surfaces comprising PMMA to form optimum PVP, P(NVP-HEMA) or PHEMA graft polymer surface modifications thereon described in U.S. Pat. No. 4,806,382 comprises carrying out the graft polymerization in an aqueous solution under specific combinations of the following conditions:

(a) monomer concentration in the range of from about 0.5 to about 50%, by weight;

(b) total gamma dose in the range of from about 0.01 to about 0.50 Mrad;

(c) gamma dose rate in the range of from about 10 to about 2,500 rads/minute; and (d) maintaining the molecular weight of the polymer in solution in the range of from about 250,000 to about 5,000,000.

The maintenance of the molecular weight of the polymer in solution at certain values, identified in U.S. Pat. No. 4,806,382, as a critical condition of the method is not actually a "condition" of the method, but rather, as stated in the specification, a result which is dependent on the reaction conditions employed in carrying out the graft polymerization process. It is, therefore, not appropriate to specify the molecular weight of the polymer in solution as a process "condition" since it is rather an outcome of the reaction conditions used in this invention and may be widely varied depending on specific gamma graft monomer-substrate-process conditions. If a certain set of fixed conditions are employed, namely: monomer, monomer concentration, total gamma dose, gamma dose rate, the molecular weight of the polymer formed in solution polymerization and radical inhibitors will be an output of the process which is dependent upon the values of the above-noted monomer, monomer concentration, total gamma dose, gamma dose rate, polymerization and radical inhibitor conditions. For example, in the presence of certain ionic monomers, solvents or radical inhibitors, solution polymerization may be inhibited significantly without sacrificing efficient surface graft polymerization and the resulting solution polymer molecular weight may thereby be relatively low (i.e., as low as 5,000–10,000).

Since the application which matured into U.S. Pat. No. 4,806,382 was filed, the inventors of the subject matter defined therein conducted additional research and unexpectedly found that although relatively low doses of 0.01 to 0.20 Mrad are generally preferred for the compositions of this patent, the process could be conducted at a total gamma dose as low as 0.001 Mrad. This improved method is described in U.S. Pat. No. 5,130,160.

The state of the art prior to the application which matured into U.S. Pat. No. 4,806,382 taught the use of relatively high gamma doses, generally greater than 0.5 Mrad, for gamma polymerization grafting and it was, therefore, surprising to find that surface grafting could be achieved at doses as low as 0.01 Mrad. The achievement of effective grafting at doses as low as 0.001 Mrad is consequently an even more unexpected result of the process of this invention. Furthermore, although grafting with monomer concentrations as low as 0.5 wt % was indicated in prior U.S. Pat. No. 4,806,382, further research has revealed that monomer concentrations as low as 0.1 wt % may be utilized in some embodiments of the graft process of this patent.

Optimally, the method may also be carried out under one or more of the following conditions:

(e) substantially excluding free oxygen from the aqueous graft polymerization solution;

(f) maintaining the thickness of the PVP or P(NVP-HEMA) surface graft in the range of from about 100 Å to about 150 microns;

(g) including a free radical scavenger in the aqueous graft polymerization solution; and (h) including in the aqueous graft polymerization solution a swelling solvent for PMMA or other polymer substrate surface.

The improved gamma irradiation induced graft polymerization of NVP, mixtures of NVP and HEMA, HEMA and other hydrophilic monomers or their copolymers on ocular implant surfaces comprising PP, PVDF, PC or PDMSO to form optimum PVP or P(NVP-HEMA) surface grafts thereon may also be carried out under specific combinations of the process parameters as indicated above for PMMA, but also under conditions which involve excluding free oxygen from the polymerization solution for preferred surface modification of these ocular implant polymer substrates.

The improved gamma irradiation induced graft polymerization of NVP, HEMA or mixtures of NVP and HEMA on plastic article surfaces to form optimum PVP, P(NVP-HEMA) or PHEMA graft polymer surface modifications thereon described in U.S. Pat. No. 4,961,954 comprises carrying out the graft polymerization in an aqueous solution under specific combinations.

As in the case of the earlier U.S. Pat. No. 4,806,382, it was also found that maintenance of molecular weight of the polymer in solution was not a "condition" of the process, but rather a result dependent upon reaction conditions.

Moreover, it was also found that although relatively low doses of 0.01 to 0.20 Mrad are generally preferred, the process can be conducted at a total gamma dose as low as 0.001 Mrad. The improved method is described in U.S. Pat. No. 5,108,776.

In U.S. Pat. Nos. 5,100,689 and 5,094,876, an improvement on the methods described in these earlier U.S. patents is disclosed. The inventions described in these applications are predicated on the discovery that the methods are significantly simplified and improved by pre-soaking the article surface to be coated in a first solution comprising the monomer prior to graft polymerizing the monomer onto the surface from a second solution of the monomer.

It is an object of the present invention to provide other improved compositions and methods for producing coatings on the surfaces of such articles; the resulting coatings having enhanced biofunctional properties.

SUMMARY OF THE INVENTION

The present invention relates to a method for modifying the surface of a material adapted for contact with tissue of a human or non-human animal to impart biofunctional, bioactive or biomimetic properties to the surface comprising:

(a) exposing the surface to a solution comprising (1) an ethylenically unsaturated monomer or mixture thereof capable, via the ethylenic unsaturation, of gamma irradiation or electron beam induced polymerization, and (2) at least one biofunctional agent; and (b) irradiating the surface with gamma or electron beam irradiation in the presence of the solution to thereby form on the surface a graft polymerized coating, the coating having physically entrapped therein or chemically bonded thereto molecules of at least one biofunctional agent which imparts biofunctional or biomimetic properties to the surface;

wherein the gamma or electron beam irradiation induced polymerization is conducted under one of the following conditions:

A.
  (i) monomer concentration in the solution in the range of from about 0.1% to about 50%, by weight;
  (ii) total gamma or electron beam dose in the range of from about 0.001 to less than about 0.50 Mrad; and
  (iii) gamma dose rate in the range of from about 10 to about 2,500 rads/min., or electron beam dose rate in the range of from about 10 to about $10^8$ rads/min.;

B.
  (i) hydrophilic monomer(s) graft under conditions which may include monomer pre-soak or plasma gamma surface modification (especially for metal or glass substrates in latter case); and
  (ii) graft polymerization of monomer(s) with bioactive/ biofunctional molecules using (i) as substrate;

C.
  (i) Hydrograft™ as in A or B above followed by dehydration and adsorption of bioactive/ biofunctional molecules into the hydrophilic polymer graft;

wherein the biological properties of the biofunctional agent are substantially maintained.

DETAILED DESCRIPTION OF THE INVENTION

Figure 1:
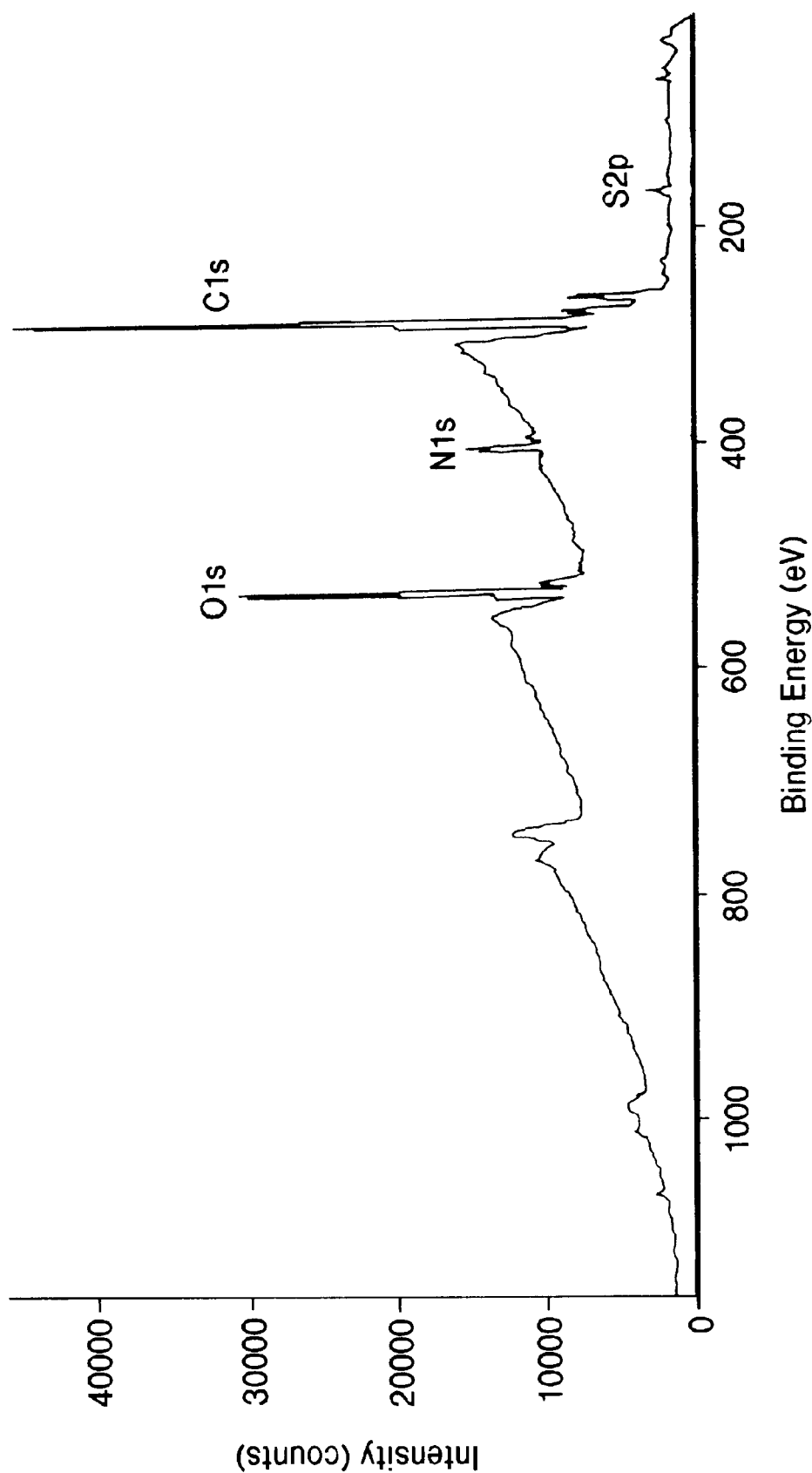
FIGS. 1–3, 9 and 10 represent FT-IR/ATR and XPS spectra for various of modified surfaces of the invention.

The entire disclosures of U.S. Pat. Nos. 4,806,382, 4,961,954, 5,094,876, 5,108,776, 5,100,689 and 5,130,160, as well as application Ser. Nos. 07/859,016 and 08/003,682 are incorporated herein by reference.

Yalon et al (supra) and Knight et al (supra) disclose gamma irradiation coatings on PMMA using N-vinylpyrrolidone (NVP) and 2-hydroxyethylmethacrylate (HEMA) and indicate inadequate dynamic (abrasive) protection of endothelium for these coatings. Dissolvable coatings of poly-vinyl-alcohol (PVA) were regarded as optimal for intraocular lenses (IOLs) by Knight et al (supra) and commercial development of a PVA-coated IOL was attempted with unsatisfactory clinical results. The gamma polymerization surface modifications reported by Knight et al (supra) and Yalon et al (supra) were carried out under process conditions of monomer concentration, solvent, dose and dose rate which were not specified and which apparently yielded poor quality, readily abraded coatings. Conditions for producing useful permanent PVP or PHEMA coatings on PMMA IOLs or any other plastic surface are not taught in the prior art. Neither Knight et al, Yalon et al or the literature on gamma-graft polymerization of the past 30 years suggests the process conditions required to achieve the complicated requirements for useful coatings on plastics. These requirements include:

(a) Thin, permanent, optically clear (in the case of contact lenses) and uniform graft coatings. The literature generally discloses conditions which produce distortion and degradation of the substrate due to the use of high gamma radiation doses (>1 Mrad) and non-aqueous solvent media, and yield thick, cloudy, non-uniform coatings [e.g., Chapiro, Radiation Chemistry of Polymeric Systems, John Wiley and Sons, Inc., New York (1962); Henglein et al, Angew. Chem., Vol. 15, p. 461 (1958)].

(b) Long-term biocompatibility in vivo.

(c) Low contact angle (high wettability) for water or underwater air bubble (less than about 30°).

(d) Non-adherent to tissue (adhesive force to endothelium less than about 150 mg/cm$^2$).

(e) Non-damaging to endothelium (less than ca. 20% damage for in vitro contact tests).

(f) Measurable graft polymer surface modification by ESCA or FT-IR analysis.

(g) Abrasion resistance by sliding (dynamic) friction testing showing no change in wetting (contact angle) and confirming before and after presence of polymer graft coating.

(h) Rapid hydration—change from dry state to wetted lubricous state on immersion in water (within five minutes).

Yalon et al (supra) disclose an in vitro technique for measuring endothelium damage. Results for PMMA were used to illustrate the method. Although it was noted that PVP coatings reduced cell damage with less damage at higher monomer concentrations, the conditions for the experiment (i.e., irradiation dose, dose rate and the like) were not disclosed, nor were any of the critical process-product relationships indicated.

The improved process conditions and parameters of the invention described in the above-noted U.S. patents and applications which are necessary to produce useful polymers having a surface modified by gamma irradiation induced graft polymerization therein of PVP, P(NVP-HEMA) or PHEMA include: % monomer, gamma dose, dose rate, penetration time or swelling time of monomer into the substrate prior to polymerization and oxygen (air) degassing. Other optimal process conditions include catalysts, free radical scavengers, polymer swelling solvents and temperature. The solution polymer molecular weight and M.W. distribution, the % conversion and residual monomer, the graft polymer thickness and surface properties and the like are process results which can change markedly as the process variables change. For example, the surface modification achieved for PVP on polymer surfaces will be different when using 10% monomer and 0.1 Mrad if prepared at low dose rates since low dose rates (slower polymerization) favor higher molecular weights. Similarly, degassed oxygen-free reaction media result in improved grafts at much lower doses. The presence of free radical scavengers such as copper or iron salts or organic reducing agents (i.e., ascorbic acid) also greatly influences other process parameters, generally reducing solution polymer molecular weight and preventing solution gelation at high monomer concentrations.

The method of the present invention is particularly applicable for the surface modification of medical instruments, devices, implants, ocular implants and contact lenses formed from a variety of plastic materials including, for example, poly-acrylates and -methacrylates (i.e., polymethylmethacrylate, polyethyl acrylate, polybutyl methacrylate and the like); polyolefins (polyethylene, polypropylene, polybutadiene); SBS (styrene-butadiene), ethylene-propylene copolymers; SE/BS (styrene-ethylene/butadiene), polycarbonates (PC), fluorocarbon polymers (i.e., polyvinylidene fluoride-PVDF, poly-tetrafluoroethylene-PTFE, polyperfluoroethylenepropylene-FEP, polysiloxanes), various aliphatic and aromatic polyurethanes, including polyurethane polyester or polyether block copolymers, polyvinylchloride and various polyesters including dacron PET (polyethyleneterephthalates). It will be understood by those skilled in the art that the method of the present invention is also applicable to mixtures, blends and copolymers of the above.

The hydrophilic graft polymer surface modifications of this invention are especially advantageous for intraocular lenses (anterior chamber, posterior chamber and phakic), but are also of great value in affording improved tissue protection and improved biocompatibility for other ocular implants, such as corneal inlays, keratoprostheses, epikeratophakia devices, glaucoma drains or shunts, retinal staples, scleral buckles and the like.

Any instrument, device, implant and the like constructed of one or more of the above materials may be surface modified according to the present invention to improve the tissue contacting characteristics of the surfaces thereof.

Plastic surgical instruments and implements such as probes, retractors, tissue and vessel separators, irrigation and aspiration tools, phacoemulsification tools, sponges, clamps, gloves, lens glides, positioning tools, forceps, insertion tools, staples, sutures and the like may be treated in accordance with the present invention.

Medical devices such as hard and soft contact lenses, intravenous and central venous catheters, laser and balloon angioplasty devices, vascular and heart devices (tubes, stents, catheters, balloons), ventricular assists, blood dialysis components, blood oxygenators, ureteral/urinary devices (Foley catheters, stents, tubes and balloons), airway catheters (endotracheal and tracheostomy tubes and cuffs), mammary implants, enteral feeding tubes, wound drainage tubes, blood bags and blood tubing may also be beneficially treated in accordance with the method of the present invention.

Implants which may be modified according to the present invention include, for example, intraocular lenses, vascular grafts and stents, soft and hard tissue prostheses (mammary, cranio/facial, tendons, joints), heart valves and artificial hearts.

Modification of these instruments, devices, implants and the like improve the surfaces thereof so as to improve blood compatibility and reduce tissue adhesion and tissue damage during surgical contact and manipulation. Moreover, the invention operates to reduce cell adhesion for reduced inflammation, reduce fibrous capsule formation for soft tissue implants, and reduce thrombogenicity and restenosis for cardiovascular devices and prostheses. Thrombogenicity (clotting) and restenosis (i.e., smooth muscle cell proliferation) which causes occlusion of vessels following angioplasty or vascular grafting (at the site of anastomoses or stents) are major problems. The incorporation of anti-clotting, anti-inflammatory and smooth muscle cell inhibiting bioactive agents into the Hydrograft™ surface modifications of this invention results in significant inhibition of these major complications associated with cardiovascular implants and devices. The invention also acts to reduce bacterial adhesion and thereby reduce the incidence of infection and further operates to reduce interfacial abrasion and friction which is of special value for joint and tendon prostheses.

Polyolefins and polyolefin/hydrocarbon block polymers are useful for constructing medical tubing, catheters, blood bags, sutures and the like. Copolymers of the SBS, EP or SE/BS type may be thermoplastic elastomers which combine rubbery properties with extrudable or injection moldable processing properties. Surface modification of such materials according to the present invention is effective in changing the normal surface characteristics of these polymers from hydrophobic to hydrophilic.

The fluorocarbon polymers are widely used for catheters (i.e., intravenous catheters), for vascular prostheses (i.e., vascular grafts) and for coating medical devices, instruments and implants due to their biocompatibility and inertness. However, the surface properties may be improved significantly according to the present invention to reduce cell and tissue adhesion and improve blood compatibility.

The silicone polymers are widely used for medical tubing and catheters, for mammary implants and other soft tissue prostheses. Hydrophilic surface modification, according to this invention, acts to reduce cell and tissue abrasion and adhesion and to thereby reduce fibrous capsule formation which is a major complication of soft tissue implants. Similarly, polyvinylchloride surface modification to produce more hydrophilic vinyl tubing and film surfaces can reduce thrombogenicity and improve biocompatibility of blood tubing, blood bags, catheters and other medical devices made of polyvinylchloride.

Polyurethanes which are used for such applications as pacer leads, intravenous catheters, enteral feeding tubes, vascular grafts and the like are also beneficially modified by the process and materials of this invention to produce more hydrophilic surfaces and make such devices more biocompatible Exemplary of suitable neutral or ionic water-soluble, hydrophilic monomers useful in the practice of the present invention are N-vinylpyrrolidone, hydroxyethylmethacrylate, acrylamide, dimethylacrylamide, polyethylene glycol monomethacrylate, hydroxypropylacrylamide, methacrylic acid, sulfopropylacrylate, styrene-sulfonic acid, 2-acrylamido-2-methyl-1-propane sulfonic acid, vinylsulfonic acid, dimethylaminoethylmethacrylate and mixtures and salts thereof.

Each of the above-described process conditions and parameters of the method of the invention may be varied within the ranges discussed below to produce certain specific combinations which are particularly advantageous for the surface modification of a particular polymeric surface.

(a) Monomer Concentration: Increasing monomer concentration increases polymer molecular weight in the graft solution and reduces contact angle (C.A.), i.e., renders the surface more hydrophilic. For example, in the case of forming PVP coatings on PMMA, in the range of from about 3–15% NVP the PMMA graft C.A. decreases from 29° to 21° at 0.1 Mrad and 309 rads/min. However, this effect is sensitive to dose rate and total dose. For example, at 1–10% NVP, but at a lower dose rate of 64 rads/min., the C.A. decreases from 49° to 18°.

In general, monomer concentrations in the range of 0.1–50% are preferred depending on other parameters. Concentrations as low as 0.1 to 0.5% at low dose rates can yield hydrophilic surface grafts with C.A. below 30–40° under conditions of this invention. At monomer concentrations greater than 20–30%, effective grafting without solution polymer gelation requires low doses and use of free radical scavengers. Monomer concentrations greater than 50% are feasible, but not preferred since high concentrations of radical scavengers must be used and polymer molecular weights and monomer conversion are lowered significantly by their use.

(b) Dose: In general, increasing total gamma dose reduces C.A. However, an important practical limit exists in that at higher doses, lower dose rates and higher monomer concentrations, reaction media become extremely viscous or form gels which are very difficult to wash and to remove (e.g., about 0.25 Mrad and 10% NVP at 309 rads/min).

It will be understood by those skilled in the art that electron beam radiation will also induce graft polymerization. Therefore, electron beam radiation of energies equivalent to that described herein for gamma radiation may be substituted for gamma radiation in the practice of the method of the invention. Electron beam voltages in the range of from about 50 KeV to about 10 MeV may be employed at currents of from about 5 mA to about 100 mA. For electron beam initiated polymerization grafting, conditions which produce dose rates substantially higher than for gamma graft polymerization, i.e., in the range of from about 10 to about $10^8$ rads/min. or more may be employed.

(c) Dose Rate: Decreasing the gamma radiation dose rate, e.g., generally increases solution polymer M.W. The C.A. also decreases correspondingly. As noted above, dose rates of up to $10^8$ rads/min. or more are practical when employing electron beam irradiation.

(d) Solution Polymer Molecular Weight: The molecular weight may vary widely depending upon process conditions, monomers and radical inhibitors used. Effective grafting with low C.A. may therefore be achieved with even low molecular weight solution polymer ($M_v$ as low as 5,000–10,000). However, solution polymer $M_v$ greater than 5,000,000 or gels which form during grafting are generally less practical because of washing problems.

(e) Degassing: Removal of oxygen from the graft solutions by a vacuum and/or an inert gas (e.g., argon purging) can have an important effect: lower total doses are required (practical grafting at less than 0.1 Mrad) and oxygen degassing can have a significant effect on $M_w$ and % conversion of monomer. For example, with degassing, good grafting of PVP on polypropylene (PP) is achieved at 0.05 Mrad and 10% NVP (C.A. 15°). Without degassing, little grafting occurs under these conditions. Oxygen degassing can be important to hydrophilic surface modification grafting where the substrate polymer is PP, PVDF or PDMSO. It has been found that graft polymerization is inefficient when using these materials as substrates in the presence of oxygen. Oxygen degassing is also beneficial for PMMA and PC substrates in that much lower radiation doses (0.01–0.15 Mrad) become effective compared with grafting these polymers in the presence of oxygen.

(f) Graft Thickness: Surface grafts less than 100–200 Å, although non-adhesive and hydrophilic, are useful but may exhibit somewhat less mechanical "softness" or compliant gel-like surfaces than thicker coatings for reduced tissue-contact trauma. Graft coatings greater than ca. 300–500 Å (or 0.03–0.05 microns) up to 50 microns or more are probably more desirable for many applications as long as they are smooth, uniform, optically clear for optic surfaces, and quickly hydrated.

Using no swelling solvents and no prolonged monomer contact with substrates prior to irradiation, surface grafts which exhibit desired properties under preferred process conditions generally may be prepared with thicknesses of about 0.1 to 5 microns. However, using swelling solvents, such as ethyl acetate with PMMA, or monomer pre-soaking, polymer grafts of 100 microns or more can be prepared. For certain applications, it may be preferred to have thicker "spongy" coatings of 10–200 microns.

(g) Free-Radical Scavengers: Free-radical traps, usually reducing agents such as $Cu^+$, $Fe^{+2}$, ascorbic acid and the like are known to inhibit radical polymerization in solution and thus be effective (especially at high gamma doses, high dose rates and high monomer concentrations) in slowing the onset of solution gelation during grafting. However, under practical grafting conditions, this may result in lower solution polymer molecular weights and high concentrations of unreacted monomer. Use of metal salts may also be objectionable where maximum biocompatibility is critical.

Although most preferred graft conditions avoid the use of radical scavengers, useful conditions for graft coatings using the water-soluble, hydrophilic monomers of this invention have also been defined using ascorbic acid to limit high viscosity and gelation of the graft polymer solution. These conditions use high monomer concentrations (up to 50%) and thicker grafts are obtained using ethyl acetate as a swelling solvent (0.5–5%).

(h) Swelling solvents: The use of substrate polymer solvents in the aqueous monomer grafting solution facilitates swelling and monomer diffusion into the polymer before and during gamma polymerization. Penetration of monomers into the substrate increases graft coating thickness and enhances bonding to the surface. Solvents such as ethyl acetate have been shown to greatly facilitate this process with some substrates such as PMMA.

Although the above-described method represents a significant improvement over prior art methods, optimum results in each case depend upon the selection of a combination of numerous process parameters, monomers and conditions.

The foregoing hydrophilic polymer grafts and method are greatly simplified and the surface grafts are significantly enhanced by another embodiment of a method of the present invention according to which the substrate to be surface-modified is pre-soaked in a grafting monomer (or mixture of monomers) or in a first aqueous solution having a concentration of from about 5% to about 95%, by weight, of the grafting monomer (or mixture of monomers) for a period of time and at a temperature sufficient to facilitate diffusion of the monomers(s) into the substrate surface. This pre-soaking step avoids the necessity for utilizing organic swelling solvents. These swelling solvents can complicate the final coating procedure since they must be completely washed away and may promote crazing or cracking of the substrate polymers.

A particular advantage of the pre-soak process is that more efficient grafting is possible under milder conditions than in those instances wherein the substrate is not pre-soaked.

The monomer pre-soaking method of the present invention results in a controlled diffusion of monomer into the substrate and may often produce what may be regarded as an interpenetrating subsurface polymer structure for the ultimately formed hydrophilic polymer graft surface modification. The latter is rendered more durable by the thus formed anchoring substructure. This monomer pre-soak improvement is also beneficially conducted with mixed monomers wherein one hydrophilic monomer is used as the pre-soak monomer and a second hydrophilic monomer is used for the subsequent gamma polymerization grafting step. This is particularly advantageous, for example, with polysiloxane surface modification wherein a first monomer pre-soak of a monomer such as N-vinylpyrrolidone (NVP), hydroxyethylmethacrylate (HEMA) or dimethylaminoethylmethacrylate (DMAEMA) followed by aqueous dimethylacrylamide (DMA) present as the medium during gamma irradiation, results in more stable, reproducible, hydrophilic surfaces for the highly flexible polysiloxane structure.

For substrates like PMMA or PDMSO, the pre-soaking is preferably conducted at a temperature of from about 25° C. to about 60° C. for from about 0.5 to about 24 hours or more (up to about 48 hours) using a first aqueous solution containing from about 5% to about 50%, by weight, of monomer(s) to achieve optimum diffusion thereof into the substrate.

Where the substrate surface is polypropylene (PP), polytetrafluoroethylene (PTFE), polyfluoroethylenepropylene (FEP), polyvinylidene fluoride (PVDF), a polycarbonate (PC), a polysulfone (PSF), a polyurethane (PUR) or a polysiloxane (PDMSO), the surface is preferably pre-soaked in the monomer(s) or a first aqueous solution containing from about 5% to about 95%, by weight, of monomer(s), at a temperature of from about 25° to about 90° C., and for from about 0.5 to about 24 hours or more (up to about 48 hours), to achieve maximum and optimum diffusion of the monomer(s) into the substrate surface.

Where mixtures of the neutral or ionic hydrophilic monomer with NVP and/or HEMA are employed to form graft copolymerized coatings, the mixtures may contain up to about 50%, by weight, of NVP, HEMA or mixtures thereof, based on the weight of the monomer mixture. However, above 20–30% HEMA, radical scavengers and low monomer concentrations should be used to prevent gelation since HEMA enhances the onset of gelation.

In general, choice of the "best" process will depend upon molecular structure of the substrate and grafting polymer and the coating thickness desired. In general, those conditions which produce extreme solution viscosities and gels or conditions which could produce solvent stress cracking or crazing of the substrates should be avoided. By way of example, the following process conditions are representative of practical conditions for the preparation of improved grafts using the monomers of this invention on various polymer substrates according to the method of this invention.

(a) For grafts on PP, PVDF and PDMSO, or combinations thereof, pre-soak the substrate in monomer at 60° C. for 4 hours followed by graft polymerization in 10% aqueous monomer with about 0.15 Mrad gamma radiation at about 500 rads/min. dose rate.

(b) For grafts on PMMA, PP, PVDF and PDMSO, or combinations thereof, pre-soak the substrate in 40% aqueous monomer at about 60° C. for 4 hours followed by graft polymerization in 10% aqueous monomer with about 0.15 Mrad gamma radiation at about 500 rads/min. dose rate.

(c) For grafts on PMMA, PDMSO and PC, or combinations thereof, pre-soak the substrate in 40% aqueous monomer at about 60° C. for about 12 hours followed by graft polymerization in 10% aqueous monomer with about 0.15 Mrad gamma radiation at about 500 rads/min. dose rate.

All percentages expressed herein, as well as in the following non-limiting examples, are by weight unless otherwise stated.

All contact angles (C.A.) and other surface characterizations for gamma or electron beam polymerization grafts, unless otherwise indicated, are for samples washed with water or water-alcohol at room temperature or elevated temperatures to remove soluble residual monomer and ungrafted polymer for the improved surface graft processes of this invention. The resulting graft polymers are stable and permanent for long-term implants and are not dissolved by aqueous media.

It will also be understood by those skilled in the art that the instruments, devices and the like to be graft coated may be also constructed of materials other than PMMA, PP, PUR, PVC, PTFE, PVDF, PC or PDMSO to facilitate their use. It will be understood by those skilled in the art that such materials may also be at least partially graft polymer surface modified so as to improve their properties. Structures of some neutral or ionic hydrophilic, water-soluble monomers useful in the practice of this invention are set forth below:

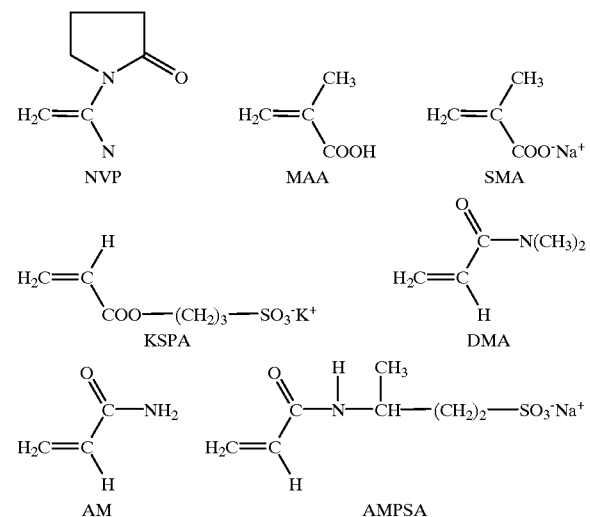

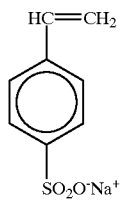

SSS

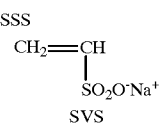

SVS

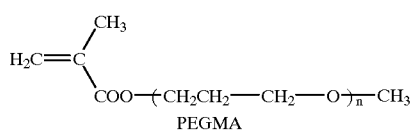

PEGMA

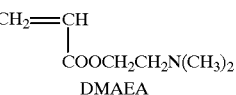

DMAEA

According to another important embodiment of the invention, the surface modification process is enhanced by a technique based on a combination of glow discharge plasma (GDP) or other ionized plasma pretreatment of the solid substrate (i.e., with radio frequency, microwave or DC plasmas), followed by low dose gamma radiation or electron beam radiation initiated grafting in the presence of polymerizable monomer(s).

Although this combination of plasma and gamma or electron beam radiation graft polymerization represents a generally improved technique for polymer substrates, it is a uniquely effective process, heretofore unavailable, for the production of polymeric surface graft modifications of metal and ceramic substrates.

Only a few attempts have been reported in literature which employed plasma treatment combined with other treatments in order to induce grafting [Bamford et al, Polymer., Vol. 2, p. 277 (1961); Bazkin et al, J. Bioeng., Vol. 2, p. 527 (1978)]. Generally, these methods are based on decomposition of surface peroxides to radicals by heat treatment which initiates graft polymerization. However, heating up to 135° C. was sometimes required [Bamford, supra]. This temperature is beyond the glass transition temperature of a large number of polymers. Therefore, such a process cannot be used for surface grafting, especially for biomedical devices such as acrylic intraocular lenses, where shape and dimensional stability are very important. In 1971, Bradley and Fales reported another process based on the plasma-induced graft copolymerization of acrylic acid onto synthetic fibers [Bradley et al, Chemtech., p. 232, April 1984]. Grafting was induced by the surface radicals present on the plasma treated fibers. The grafting yields were generally relatively low and no grafting of other monomers was attempted. In contrast, the combined use of GDP surface modification with gamma graft surface modification represents a novel method for the preparation of improved polymer graft surfaces on polymers, metals and ceramics.

According to the combined technique, a material surface capable of forming activated sites upon exposure to GDP is exposed to GDP such as RF-GDP or microwave GDP of sufficient power for a time required to activate and/or excite the surface of the material and, optionally, subsequently the surface is exposed to air or oxygen to thereby form peroxy or hydroperoxy groups or other chemically reactive atomic or molecular species on the surface, followed by subjecting the thus activated surface to the above-described gamma or electron beam irradiation graft polymerization step.

GDP treatment of the surfaces of materials followed by gamma or electron beam radiation induced polymerization surface modification, wherein the reaction parameters of each are carefully controlled, can be applied to a surprisingly wide variety of materials to alter the surface characteristics thereof without affecting the bulk or other properties of the material. Moreover, the method is relatively simple to operate and is highly efficient and economical.

The combined method produces materials heretofore unknown which possess combinations of bulk and surface properties which render them invaluable in constructing articles having numerous uses.

On the other hand, the combined plasma/gamma process of the invention is unusual and surprisingly practical and effective for surface polymer grafting of polymers, metals and ceramics yielding uniform polymeric surface modifications with minimal solution polymerization complications. This is due to the fact that the plasma surface treatment activates and induces grafting sites which are available for subsequent surface graft polymerization by gamma irradiation. Thus, compared to gamma graft polymerization alone on polymer substrates, grafting will occur more readily and more extensively because of the prior plasma activation and permits gamma grafting under mild conditions without substantial solution polymerization. Moreover, for metals and ceramics which are resistant to effective surface graft polymerization, the initial plasma activation uniquely creates surface grafting sites for subsequent gamma graft polymerization which has heretofore been difficult to achieve.

It will be understood by those skilled in the art that any surface may be modified according to the method of the invention provided that, when exposed to GDP under the conditions described herein, activated surface species or sites such as ions or radicals are formed therein which will bond with the polymers and copolymers graft polymerized thereon under the gamma or electron beam irradiation conditions described herein. It will be further understood that, in some instances, the activated sites formed on the surface by GDP may be advantageously exposed to oxygen to form chemically reactive atomic or molecular species or sites therein, such as peroxy or hydroperoxy groups, suitable for covalent bonding and graft copolymerization under requisite gamma or electron beam irradiation conditions.

Any instrument, device, implant and the like constructed of one or more plastic, ceramic or metallic material component may be surface modified according to the present invention to improve the tissue contacting and biofunctional characteristics of the surfaces thereof.

Each of the above-described process conditions and parameters of the method of the invention may be varied within the ranges discussed to produce certain specific combinations which are particularly advantageous for the surface modification of particular materials or combinations of materials.

The combined plasma-gamma surface modification process and coatings of this invention are uniquely applicable to metallic, ceramic or glass instruments or devices which are less readily chemically surface grafted than polymeric substrates.

It will be understood by those skilled in the art that the present invention is applicable to the treatment of any surface capable of oxidation or activation by GDP and formation of reactive sites due to the GDP and/or exposure of the activated surface to oxygen. Thus, the method is applicable to metallic, polymeric or ceramic materials.

Typical metallic surfaces which may be treated according to the method of the invention include iron and iron alloys including various alloy steels, nickel, copper, cobalt, tantalum and a wide variety of metallic alloys.

Suitable polymeric substrates include polyacrylates and -methacrylates (i.e., polymethylmethacrylate, polyethylacrylate, polybutylmethacrylate and the like);

polyolefins (polyethylene, polypropylene, polybutadiene); SBS copolymers (styrene-butadiene); ethylene-propylene copolymers; SE/BS (styrene-ethylene/butadiene-styrene) block copolymers; polycarbonates (PC); fluorocarbon polymers (i.e., polyvinylidene fluoride-PVDF, polytetrafluoroethylene-PTFE, polyperfluoroethylene-propylene-FEP); polysiloxanes; various aliphatic and aromatic polyurethanes, including polyurethane polyester or polyether block copolymers; polyvinylchloride; various polyesters including polyethylene terephthalate (PET); polycarbonate/polydimethylsiloxane copolymers (PC/PDMSO) and the like.

Inorganic glasses and ceramics of various compositions such as silica, soda glass, borosilicate glass, high calcium and phosphate glasses, quartz and the like may be utilized according to the present invention.

The invention is particularly adapted for the construction of polymeric, ceramic or metallic biomedical articles and articles which comprise two or more such materials such as surgical instruments and implements such as probes, retractors, tissue and vessel separators, irrigation and aspiration tools, phacoemulsification tools, sponges, clamps, gloves, lens glides, positioning tools, forceps, insertion tools, staples, sutures and the like, all of which may be treated in accordance with the present invention.

It will be further understood by those skilled in the art that the conditions employed in the GDP treatment such as that using RF-GDP will depend upon the particular surface being treated. Generally, however, exposure of the surface to RF-GDP at a power in the range of from about 1 W to about 500 W or more for a time period of from about 1 second to about 30 minutes will usually be sufficient to activate or oxidize the surface.

Figure 11:
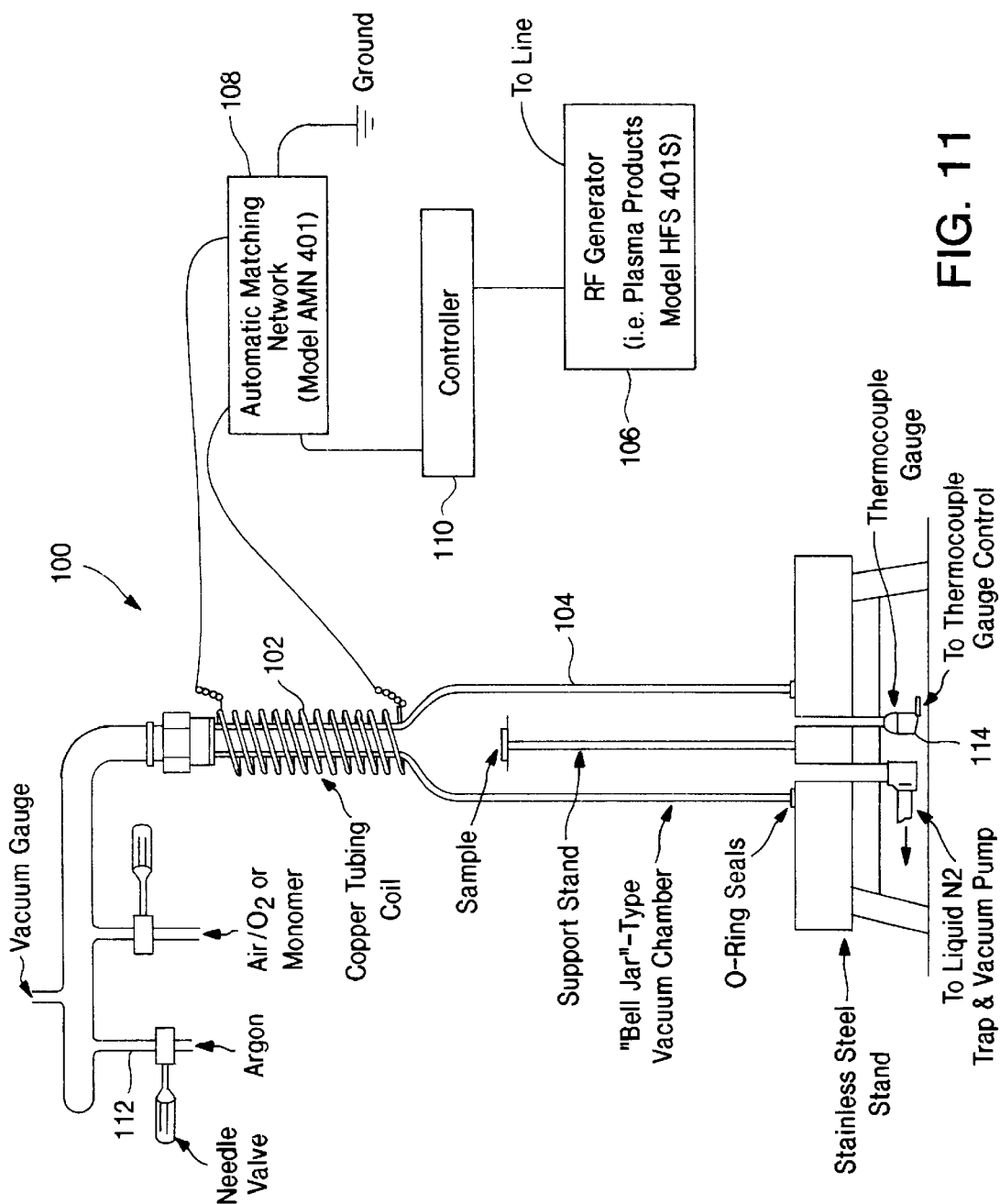
FIG. 11 is a schematic drawing of a RF plasma apparatus for carrying out an embodiment of the invention.

Any conventional GDP generating system such as radio frequency (RF), microwave, or DC discharge system may be used in the practice of the invention. RF-GDP is used to illustrate one preferred embodiment of the practice of this invention for GDP activation of metal, ceramic or polymer surfaces prior to gamma radiation graft polymerization. RF-GDP treatments are typically carried out in a system such as that schematically represented in FIG. 11 by reference numeral 100. A copper coil 102 is wound around a portion of the pyrex vacuum chamber reactor 104 to excite a GDP. The system illustrated used a 13.56 MHz RF generator 106 (Model HFS 40155, RF Plasma Products, Inc.) rated to 500 W. The coil and generator are matched using a matching network 108 (Model AMN-502, RF Plasma Products, Inc.) and controller 110. The system is typically evacuated to $10^{-4}$ Torr or less via a vacuum pump (not shown) and the glow discharge established with argon (or any other suitable gas) introduced via inlet 112 increasing the pressure to about 0.2 Torr. Time (seconds to minutes) and power (1 W to 500 W) are readily varied. The temperature of the system is monitored by thermocouple 114.

Exposure of the activated surface to oxygen, air or water vapor can result in the formation of surface peroxy and/or hydroperoxy groups to facilitate subsequent graft polymerization.

The crux of the present invention resides in the discovery that, in addition to the advantageous hydrophilic biophysical tissue and cell non-adherent properties imparted to tissue-contacting surfaces by the methods described above, the surfaces may also be modified so as to exhibit biofunctional or biomimetic properties by incorporating various bioactive, biofunctional and natural tissue constituent biomolecules into the Hydrograft™ surface modification by (a) including in the solution of graft polymerizable monomer(s) a biofunctional agent which becomes physically entrapped in or chemically bonded to the gamma or electron beam induced graft polymerized surface, or (b) adsorbing and/or reacting a biofunctional agent into the Hydrograft™ surface modification after forming the Hydrograft™ coating.

By the term "biofunctional agent" is meant any biologically active material, i.e., an agent which exerts a physical, chemical or desired physiological effect in tissue of a human or non-human animal, which agent or biological effect is retained to a significant degree in the Hydrograf™ composition under the conditions of the graft polymerization process of the invention or during post-forming impregnation of the Hydrograft™ surface modification.

The biofunctional agent is selected such that its exposure to tissue in the graft polymerized surface produces desired bioactivity or biomimetic properties in the surface modified material.

By the term "biomimetic" is meant the mimicry of the biological or physiological properties of the biofunctional agent or of natural tissue surfaces by the graft polymerized surface in which the agent is embedded or bonded.

There are two general types of biofunctional surfaces with which the present invention is concerned. One such class includes those biomolecular surfaces which are "biomimetic" or mimic the structural, chemical or physical qualities of tissues or natural materials and thereby function more effectively in a biological environment without, for example, triggering adverse reactions therein.

The second class of biofunctional surfaces embraces surfaces designed to effect chemical or physical changes in the biological environment in which they are placed, for example, cytotoxic anti-tumor activity, immune system modulation or stimulation, anti-bacterial, anti-inflammatory, growth hormone (growth factor), bioaffinity cell or metabolite receptor response, promotion of tissue growth or wound healing, or the like.

The unifying concept of the present invention is the tailoring of the surface properties of biomolecular materials to produce a desired biological behavior or response when the material is contacted with tissue of a human or non-human animal while retaining the bulk properties of the material.

The method of the present invention enables such a tailoring of the surfaces of biomaterials by the physical and/or chemical incorporation of natural and synthetic biofunctional. agent molecules into simple or interpenetrating (IPN-type), preferably hydrophilic, surface graft polymerized network coatings employing the gamma or electron beam induced graft polymerization process described herein. The synthesis of the invention combines (1) versatility for a wide variety of medical polymer substrates and graft polymer compositions, (2) unique utility for a wide variety of complex shapes of biomedical implants and devices wherein internal structures (i.e., the lumens of tubes) or highly irregular geometries may be uniformly surface modified, (3) very mild aqueous reaction conditions to enable physical entrapment or covalent binding of even labile bioactive molecules into highly hydrated graft matrices without loss of bioactivity, and (4) a process which enables good control of graft thickness, IPN structure, composition and access of the biofunctional molecules to the surrounding physiological environment.

The method of the invention is an improvement upon the previously described gamma and electron beam induced graft polymerization surface modification methods in that it utilizes the gamma or electron beam radiation graft processes with monomers in a novel way. Specifically, it has been discovered that the low temperature, aqueous solution, low radiation dose process enables one to incorporate a wide variety of individual and mixed drugs, proteins, polysaccharides and other bioactive or biofunctional molecules into the hydrophilic surface graft polymer with retention of the properties of the incorporated molecules. The graft polymer, which may be based on any of the neutral or ionic monomers previously disclosed (e.g., PVP, DMA, acryloyl-PEG, KSPA and the like), thereby acts as a permeable, aqueous matrix for the added biofunctional molecules, biopolymers or drugs. Even very complex mixtures which simulate the composition of natural tissue/cell membranes may thereby be prepared to achieve biomimetic surface properties for implants and devices and to provide surfaces which may also exhibit enhancement of certain desired properties (i.e., anti-bacterial, anti-inflammatory, non-thrombogenic, restenosis inhibition, enhanced vascular endothelialization, etc.). These complex biofunctional surfaces may be achieved by (1) incorporation of the bioactive molecules into the graft polymerization solution or by (2) physical or chemical incorporation of the bioactive molecules into the graft after the formation of the surfaces.

Exemplary of monomers for forming the biomimetic graft polymerized surfaces are:

| | |
|---|---|
| NVP | N-vinylpyrrolidone |
| HEMA | Hydroxyethylmethacrylate |
| MAA | Methacrylic acid |
| MAA-co-NVP | Methacrylic acid-co-(N-vinyl pyrrolidone) |
| SMA | Sodium methacrylate |
| SMA-co-NVP | Sodium methacrylate-co-(N-vinyl pyrrolidone) |
| KSPA | Potassium sulfopropyl acrylate |
| SSS | Styrene sulfonic acid, sodium salt |
| AMPSA | 2-acrylamido-2-methyl-1-propane sulfonic acid |
| AM | Acrylamide |
| DMA | Dimethylacrylamide |
| DMAEMA | Dimethylaminoethylmethacrylate |
| PEGMA | Methoxy polyethylene glycol monomethacrylate |
| NVP-co-SMA-co-AMPSA | N-vinyl pyrrolidone-co-sodium methacrylate-co-(2-acrylamido-2-methyl-1-propane sulfonic acid) |

Suitable biofunctional agents for inclusion in the biofunctional or biomimetic surface compositions include: hirudin and polysaccharides such as heparin or aldehydeheparin (for anti-clotting and smooth muscle cell inhibition), chondroitin sulfate, hyaluronic acid and carboxymethylcellulose; plasma, tissue and basement membrane proteins such as albumin, collagen, laminin, elastin and fibronectin; and various enzymes, including those with proteolytic, thrombolytic, esterolytic, oxidative, anti-inflammatory, anti-clotting, anti-oxidant, wound healing and immune system activity, including, for example, tPA, streptokinase, urokinase, glucose oxidase, superoxide dismutase, catalase, plasmin, trypsin and the like; anti-bacterial drugs such as gentamicin, streptomycin, tobramycin, penicillin, tetracycline, floxins and the like; anti-inflammatory drugs such as corticosteroids and NSAID such as cortisone, prednisone, ibuprofen, etc.; growth factors such as epidermal and endothelial cell growth factors; cytotoxic and anti-tumor drugs such as Novantrone™, Adriamycin™, methotrexate, ARA-C, cis-platin and the like; polypeptides which exhibit specific receptor binding functionality for antigens, antibodies, cell membrane receptor sites, T-cells, B-cells including, for example, the RGD fibronectin peptide sequence (ARG-GLY-ASP) and REDV (ARG-GLY-ASP-VAL) C-terminal dodecapeptide of the fibronectin gamma chain which mediate platelet adhesion; cell membrane polysaccharide binding proteins such as the lectins (e.g., concanavalin-A) and the like; beta-blockers and carbonic anhydrase inhibitors such as timolol, methazolamide and the like; anti-inflammatory anti-oxidants such as mannitol, glutathione, ascorbic acid and the like; cell membrane phospholipids such as various natural phosphatidyl cholines (PC), PLs such as PL glycerol, distearyl-PL (some in combination with cholesterol and hydrophilic gangliosides such as GM-1) and the like, as well as polymerizable acetylenic or vinyl functionalized PLs such as MPC (2-methacryolyloxyethyl phosphoryl choline), HEMA-PL (bis-[methacryloxyethylene]-L-α-phosphatadylcholine), 12-PL (12-bis-[methacryloyloxydodecanoyl]-phosphatadyl choline), and the like which may be copolymerized into the hydrophilic vinyl polymer surface modification structure; various hormonal or cell membrane constituent immune modulators such as myramyl dipeptide and its deacylated derivatives (e.g., 3-MPL), various BCG cell wall constituents; various bioactive bacterial and human cell wall components; and even biofunctional living cells such as pancreatic islet cells, endothelial and epithelial cells, and the like.

The most preferred embodiment of the method of the present invention is that wherein the gamma or electron beam irradiation induced polymerization process described above is conducted in multiple steps. The first step comprises conducting steps (a) and (b) under conditions (i), (ii) and (iii) in the absence of any biofunctional agent. The second step comprises soaking the product of the above first step in a solution of at least one biofunctional agent, the soaking being conducted for a period of time and at a temperature sufficient to facilitate diffusion of at least one biofunctional agent into the polymerized surface. A final step comprises conducting steps (a) and (b) of claim 1 under conditions (i) and (iii), but wherein the total gamma or electron beam dose (ii) is in the range of from about 0.001 to less than about 0.20 Mrad.

Of course, the above-described pre-soaking step (i.e., wherein prior to any graft polymerization step, the surface is pre-soaked in a solution of the monomer) may also be carried out in connection with the just-described multiple step graft polymerization method.

Although aqueous media are generally preferred, various polar solvents for the biofunctional component(s) which may also be employed to prepare the biofunctional agent soaking solution include dimethylsulfoxide, dimethylformamide, tetrahydrofuran, etc., including aqueous mixtures as well as other polar organic solvents.

The concentration of the biofunctional agent in the soaking solution may range from about 0.001% to about 50% by weight based on the vinyl monomer concentration.

Preferably, the soaking step is conducted at a temperature of from about 4° to about 90° and for a time between about 5 minutes and about 24 hours.

It is also understood that the method and hydrophilic polymer graft surface modification compositions of this invention may incorporate not only biofunctional, bioactive or biomimetic compounds and macromolecules, but may also be used to incorporate cell walls, tissues and even living, inactivated or dead whole cells which may afford biofunctional qualities to the surface modifications of this invention (i.e., insulin production and glucose regulation using pancreatic islets, immunological and vaccine behavior using inactivated viral and bacterial components, and the like).

The invention is illustrated by the following non-limiting examples.

EXAMPLE 1

Two-Step (Pre-Soak) Graft

Although a one-step simultaneous radiation graft polymerization process using monomer-biofunctional agent solutions is feasible with many biofunctional molecules, employing a pre-soak/two-step irradiation technique minimizes the possibility of radiation damage to bioactive agents which may be radiation-sensitive since it enables irradiation-induced graft polymerization under milder conditions (less than about 0.2 Mrad) in the presence of the bioactive agent. The following procedure is typical of the general method employed when utilizing the pre-soak/two-step method of the present invention.

Pre-Soak
  (a) Pre-soak in 40% NVP at 60° C. for 4 hrs.
  (b) Immediately transfer to 15% NVP and degas.
  (c) Gamma irradiate to 0.09 Mrad at 701 rads/min.
  (d) Remove substrate from the solution, rinse with distilled water and then dry to constant weight at 60° C. under vacuum.

Graft Polymerization
  (a) Put dried pre-grafted substrate in a solution of the monomer and other biofunctional components (i.e., heparin, chondroitin sulfate, albumin, collagen, laminin, gentamicin, and the like) to be incorporated into the graft.
  (b) Degas.
  (c) Gamma irradiate to 0.06 Mrad.
  (d) Remove samples from the solution, wash and dry to constant weight.

Composite polyelectrolyte surfaces having carboxylate, amino and sulfonate groups can mimic the structure and behavior of certain biomolecules (i.e., heparin, chondroitin sulfate, albumin and the like) or the surfaces of biological membranes which are known to play important roles in biological interfacial reactions. Multi-component/multi-functional graft systems have not heretofore been prepared using radiation grafting. One preferred grafting method used first involves a "pre-soak" to graft copolymerize monomers such as DMA, NVP, SMA and AMPSA on PMMA, PDMSO or other substrates. A second step in this two-step grafting method graft polymerizes a monomer mixture with bioactive agent, for example, NVP and the biofunctional agent molecule heparin on the substrate. The radiation grafting of the NVP/heparin system is far simpler and cleaner than previously reported chemical methods for surface binding of heparin on medical device materials. Most important, radiation graft copolymerization incorporation of heparin with a non-biodegradable, yet biocompatible, polymer (i.e., PVP) enhances the biostability of the biofunctional molecule with substantial retention of the anti-thrombogenic bioactivity of heparin in this example.

(PVP-co-PSMA-co-PAMPSA)-g-PMMA

A multi-component polyanionic graft involving NVP, SMA and AMPSA on PMMA was prepared. The monomer ratios, experimental conditions and results are given in Tables 1 and 2. Gravimetric analysis shows that under pre-soak conditions, a higher graft yield is obtained. Under the pre-soak conditions, the contact angle was decreased to 35°, indicating that a more hydrophilic surface is obtained as compared to the surface of unmodified PMMA (contact angle of 65–70°).

TABLE 1

Gravimetric Data For (PVP-co-PSMA-co-PAMPSA)-g-PMMA
(Grafting In 20 wt % NVP/SMA/AMPSA In A 2/1/1 Ratio
With A Dose Of 0.15 Mrad)

| Pre-Soak Conditions | Graft Yield (wt %) | Contact Angle (°) |
| --- | --- | --- |
| (a) | 0.1 | 45 |
| (b) | 0.1 | 45 |
| (c) | 0.2 | 35 |
| (d) | 1.5 | 27 |

(a) No pre-soak
(b) Pre-soak in actual grafting solution at 25° C. for 24 hrs.
(c) Pre-soak in actual grafting solution at 60° C. for 4 hrs.
(d) Pre-soak in 40% NVP at 60° C. for 4 hrs., then transfer to 20 wt % NVP/SMA/AMPSA (2/1/1 ratio) prior to gamma irradiation.

TABLE 2

XPS Data For (PVP-co-PSMA-co-PAMPSA)-g-PMMA
(Grafting In 20 wt % NVP/SMA/AMPSA In A 2/2/1 Ratio
With A Dose of 0.15 Mrad)

| Pre-Soak Conditions | % Atomic Concentration | | | |
| --- | --- | --- | --- | --- |
| | C1s | O1s | N1s | S2p |
| (a) | 77.0 | 23.7 | 0.6 | 0.0 |
| (b) | 76.4 | 22.8 | 0.8 | 0.0 |
| (c) | 75.9 | 18.9 | 3.8 | 1.4 |

(a) No pre-soak
(b) Pre-soak in actual polymerizing solution (i.e., 20% NVP/SMA/AMPSA in a 2/1/1 ratio) for 24 hrs. at 25° C.
(c) pre-soak in 40% NVP at 60° C. for 4 hrs.

Pre-soaking of the substrate in 40% NVP at 60° C. for 4 hours prior to gamma irradiation in the ternary monomeric solution produces a higher grafting yield and more hydrophilic surface (contact angle decreases to 27°).

XPS analysis provides clear evidence that a complex polyanionic graft copolymer is obtained on the PMMA surface. This is demonstrated by the appearance of N1s and S2p peaks at 401 eV and 167 eV, respectively, as seen in FIG. 1. The N1s and S2p peaks arise from graft copolymerized NVP and AMPSA.

XPS results (FIG. 1 and Table 2) suggest that the pre-soak process is preferred for higher yield grafts according to conditions shown in Table 2. The appearance of N1s and S2p peaks also clearly indicates that a multi-component graft is obtained. This graft system is particularly useful with incorporated biofunctional molecules (i.e., gentamicin, laminin, collagen, etc.) which are added at concentrations of 1–20 wt % of monomers in the second step graft monomer solution.

(PVP-co-Heparin)-g-PMMA

Heparin is an extremely effective anti-coagulant which blocks the formation of fibrin by complexing AT3 (anti-thrombin III) prothrombin and is also an inhibitor for vascular smooth muscle cell proliferation. Thus, heparin has been widely studied for modification of blood contacting materials. Heparin is also a potentially potent agent for inhibiting fibroblast growth and controlling ocular scarring and membrane formation which can cause post-cataract surgery lens opacification. In ocular surgery, inhibition of lens epithelial cell adhesions and proliferation is sought to improve the long-term bibcompatibility of IOL implants.

Many studies have been reported on the binding of heparin to synthetic polymers. for use in blood contacting devices; however, the radiation grafting of heparin according to the present invention represents a unique concept. Other methods for heparinization of materials may be categorized as: (i) ionic binding or adsorption and (ii) covalent binding of heparin onto polymers through coupling agents.

The aim of the method of the present invention is to provide a novel alternative approach which would accomplish the incorporation of heparin into surface grafts of superior biostability. The grafting method of this example was the "pre-soak method" which involved a two-step irradiation. The first step involved formation of a PVP pre-graft which was then followed by post-graft copolymerization of NVP-co-heparin onto PMMA. The experimental conditions are given in Table 3.

Table 4 shows the gravimetric and contact angle results for the different grafting conditions employed in this example of the present invention. From these data, two general trends can be distinguished. First, the presence of heparin in the polymerizing solution actually improves the graft yield even without pre-soaking. Second, under pre-soaking conditions, higher grafting yields are generally obtained.

TABLE 3

Conditions For The Two-Step Radiation Grafting Of (NVP-co-Heparin) On PMMA

| Step I | Step II |
| --- | --- |
| (a) Pre-soak in 40% NVP/60° C./4 hrs. | (a) Transfer pre-grafted sample to 15% NVP/heparin |
| (b) Transfer to 15% NVP | (b) Irradiate to 0.06 Mrad |
| (c) Irradiate to 0.09 Mrad | (c) Wash and dry |
| (d) Wash and dry | |

TABLE 4

Data For Radiation Grafting Of (NVP-co-Heparin) On PMMA

| NVP/Heparin (Wt %) | Ratio | Graft Yield (wt %) | Contact Angle (°) | Pre-Soak Conditions |
| --- | --- | --- | --- | --- |
| 15.0 | 1:0 | 2.5 | 20 | 40% NVP/60° C./4 hrs. |
| 15.0 | 100:1 | 2.9 | 20 | 40% NVP/60° C./4 hrs. |
| 15.0 | 10:1 | 3.4 | 20 | 40% NVP/60° C./4 hrs. |
| 15.0 | 2:1 | 4.8 | 20 | 40% NVP/60° C./4 hrs. |
| 15.0 | 1:1 | 5.0 | 20 | 40% NVP/60° C./4 hrs. |
| 15.0 | 1:0 | 0.3 | 20 | No pre-soak |
| 15.0 | 100:1 | 0.5 | 20 | No pre-soak |
| 15.0 | 10:1 | 0.5 | 20 | No pre-soak |
| 15.0 | 2:1 | 0.5 | 20 | No pre-soak |
| 15.0 | 1:1 | 0.5 | 20 | No pre-soak |

Figure 2A:
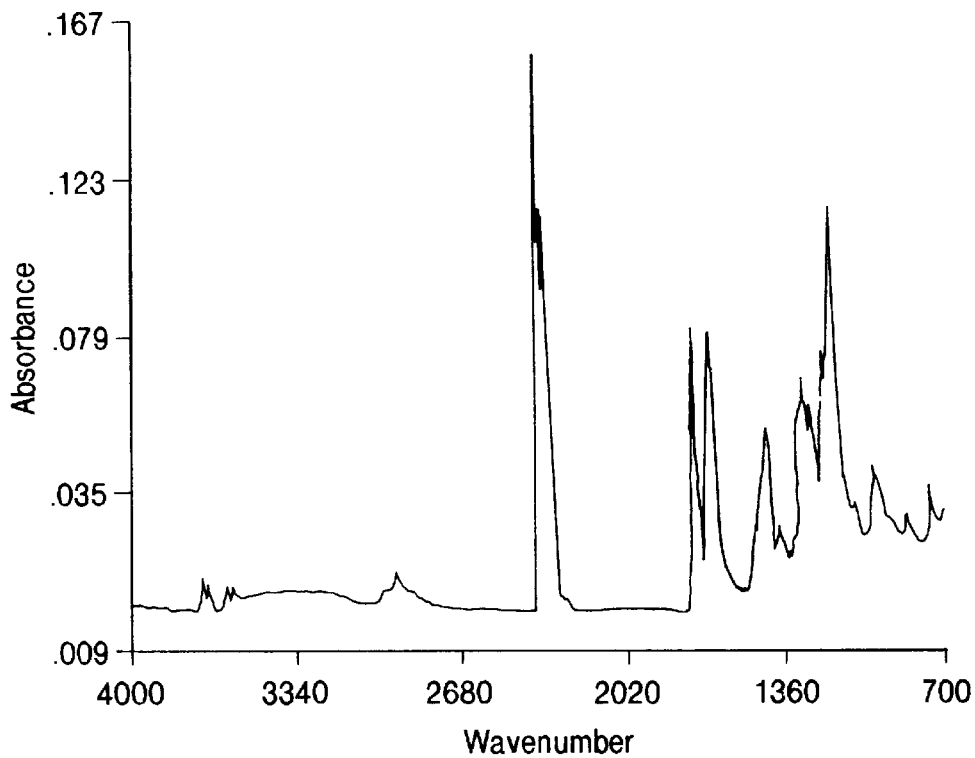
Figure 2B:
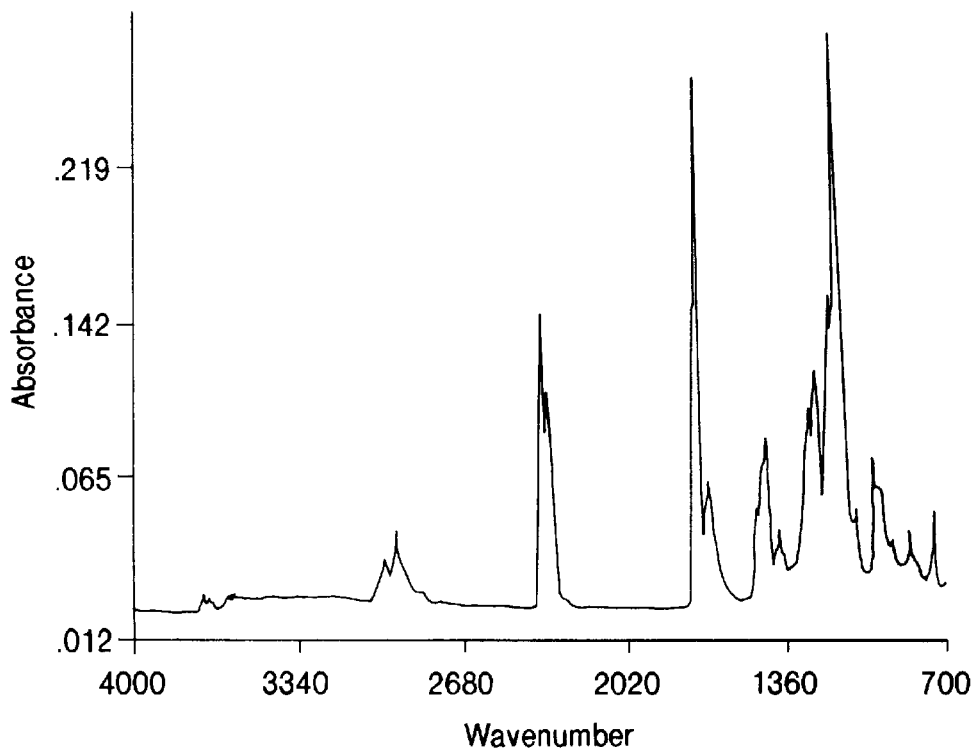

FIGS. 2a and 2b show typical FT-IR/ATR spectra for PVP-g-PMMA and (PVP-co-heparin)-g-PMMA, respectively. The two-step grafting process was used in both cases, as described in Table 3. Comparison of the carbonyl regions of these two figures shows a clear distinction between the two samples. The intensity of the carbonyl peak around 1660 $cm^{-1}$ is much higher when heparin is incorporated into the grafting solution, as compared to grafting with NVP alone under similar conditions, indicating that efficient grafting of PVP-co-heparin is obtained.

Figure 3:
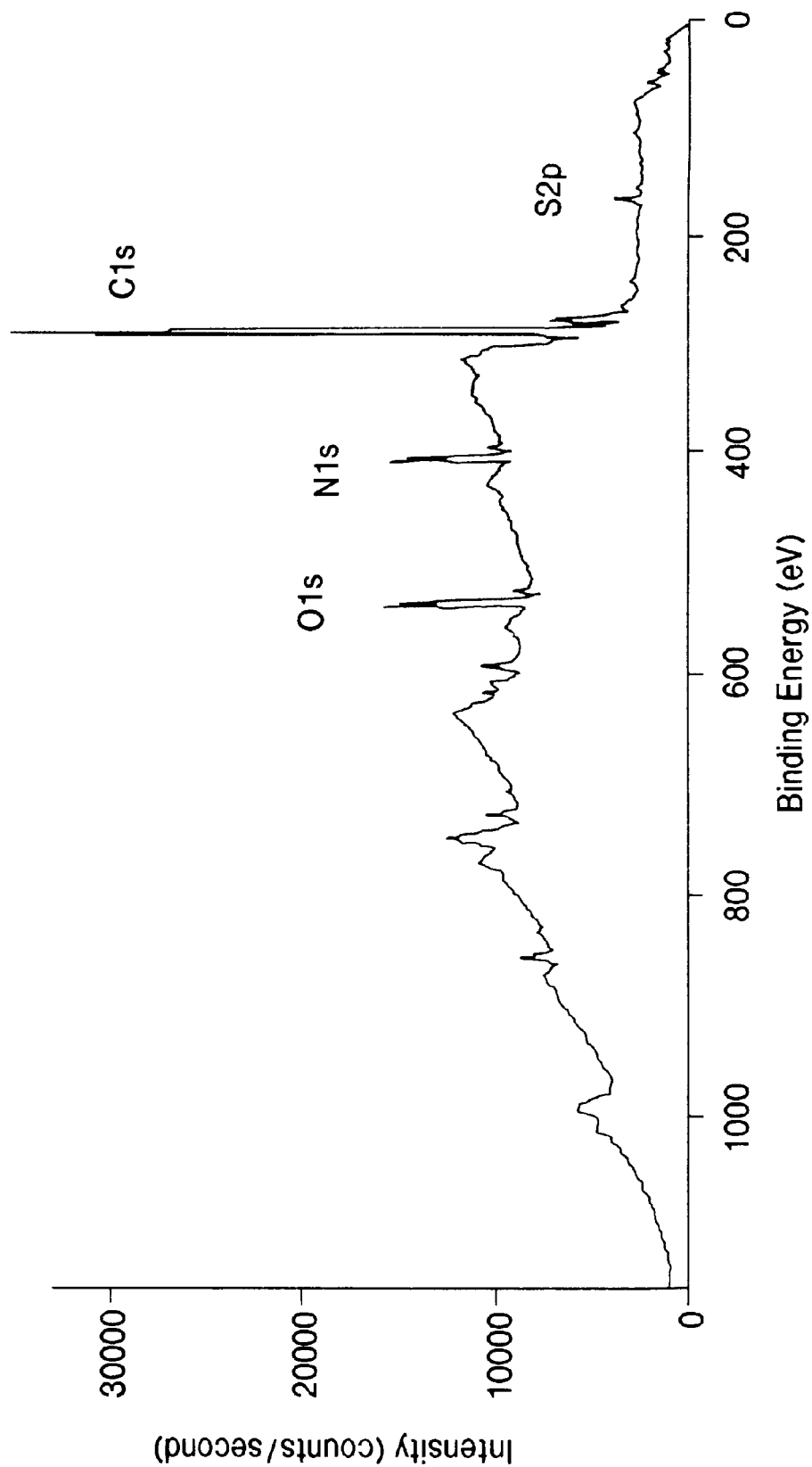

Further evidence for incorporation of heparin in the graft on PMMA is provided by XPS analysis, as shown in FIG. 3. In addition to a relatively intense N1s peak at 401 eV arising from PVP, an S2p peak appears at 167 eV, which is due to the heparin sulfur atoms.

EXAMPLE 2
Surface Modification of Vascular Graft Prostheses and Stents
Hydrophilic Surface Grafts on PMMA
A Model Substrate for Evaluating Vascular Endothelial Cell Growth and Platelet Adhesion This example illustrates the synthesis and characterization of various hydrophilic surface grafts of various functionalities on PMMA using the gamma induced graft polymerization method. The effect of these surfaces on bovine vascular endothelial cell adhesion and growth and their effect on human platelet adhesion are assessed. The beneficial effects of complex grafts incorporating various biological proteins or combinations of monomers on endothelial cell and platelet adhesion is indicated.

Materials
1. Substrate: PMMA
2. Monomers: the following monomers were investigated for surface grafting on PMMA:

| NVP | (N-vinyl pyrrolidone) |
| --- | --- |
| DMA | (Dimethylacrylamide) |
| KSPA | (Potassium sulfopropyl acrylate) |
| DMAEMA | (Dimethylaminoethylmethacrylate) |
| CMC | (Carboxymethyl cellulose) |
| AMPSA | (2-Acrylamido-2-methyl-1-propane sulfonic acid) |
| SMA | (Sodium methacrylate) |
| TRI | (10% NVP, 5% SMA, 5% AMPSA) |

3. Biofunctional Molecules: the following proteins were incorporated into the surface Hydrograft™ matrix:

| LM | Laminin |
| --- | --- |
| FN | Fibronectin |
| ALB | Albumin |

Sample Cleaning and Preparation
1. Samples 8 mm×8 mm were cut from sheets of medical grade PMMA (Perspex).
2. All samples were cleaned by sonication in 0.1% aqueous Triton-X 100 solution (1×20 min.) in ultra-pure water (3×20 min.), then dried under vacuum at 60° C.

Gamma Grafting—One-Step Method
1. Samples were pre-soaked in 40% NVP at 60° C. for 4 hours.
2. The pre-soaked samples were transferred to appropriate monomer solutions and degassed with argon prior to gamma irradiation.
3. Gamma irradiation was carried out at 590 rads/min. to various doses.
4. Samples were washed for 3 days with 3–4 changes of water per day.

Gamma Grafting—Two-Step Method—Surfaces Incorporating Biofunctional Proteins
1. Samples were pre-soaked in 40% NVP at 60° C. for 4 hours.
2. The pre-soaked samples were transferred to 15% NVP solution and degassed with argon prior to gamma irradiation dose.
3. Gamma irradiation was carried out at 590 rads/min. to a total dose of 0.09 Mrad.
4. Samples were washed and stored in a desiccator.
5. Samples were transferred to monomer/bioactive molecule solutions and degassed with argon.
6. Samples were then gamma irradiated to 0.06 Mrad at 590 rads/min.
7. Samples were washed for 3 days with 3–4 water changes per day.

All Methods
Samples were dried under vacuum and stored in a desiccator.

Surface Characterization
(a) X-ray Photoelectron Spectroscopy (XPS) using a Kratos XSAM 800 spectrometer operating typically at 12 Kv, 20 mA and $10^{-8}$ Torr.

(b) Infrared spectroscopy (FT-IR/ATR) using a Nicolet 60 SX spectrometer and a KRS-5 internal reflecting crystal.
(c) Contact angle measurements using a goniometer and captive air bubble technique.

In Vitro Studies
1. Biocompatibility was assessed by exposing samples to bovine vascular endothelial cells and human platelet solutions of 20,000 cells/mm$^3$ each.
2. Samples were incubated for 8 hours and adhesion was measured by radioisotope labeled cells and platelets.
3. Comparisons were made by relating the number of counts per minute of unmodified PMMA to surface modified PMMA samples.

Surface Characterization Results
Both XPS and IR analysis confirm the formation of a hydrophilic surface graft greater than ca. 1 micron in thickness. XPS and IR also show the presence of incorporated biofunctional molecules in the surfaces, as noted by shifts in stoichiometric ratios and peak broadening. Contact angle measurements showed a decrease in contact angle for all grafts:

| Monomer | Contact Angle (°) |
|---|---|
| unmodified PMMA | 70 |
| 10% PVP | 20 |
| 10% KSPA | 21 |
| 10% AMPSA | 21 |
| 10% DMA | 20 |
| 20% TRI | 27 |

Figure 4:
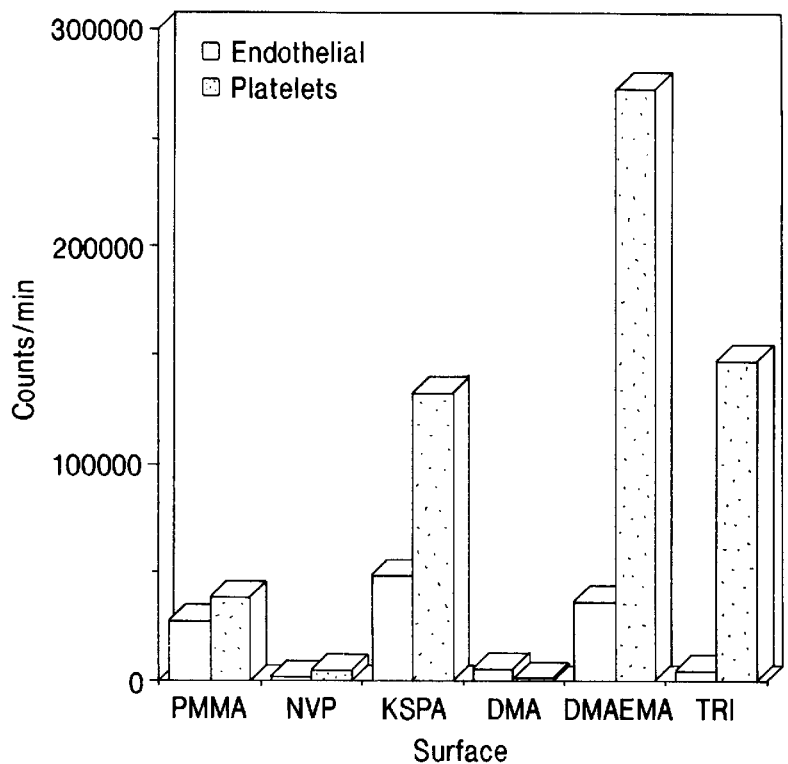
FIGS. 4–8 depict cell culture data demonstrating endothelial and platelet cell adhesion to various modified surfaces.
Figure 5:
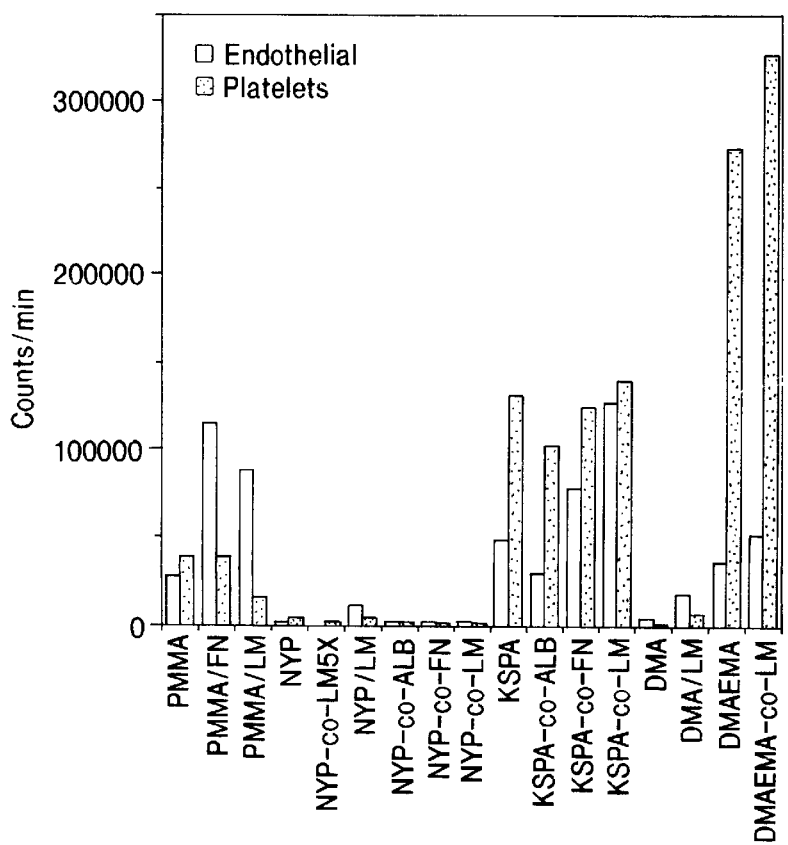

In Vitro Results
Cell culture data (FIGS. 4 and 5) show that PVP grafts had the lowest endothelial and platelet cell adhesion and cationic DMAEMA had the most cell adhesion. DMA showed an exceptional affinity for endothelial cells over platelets, which is a desirable property for blood contacting surfaces since one desires low thrombogenicity, but a propensity for endothelialization.

Figure 6:
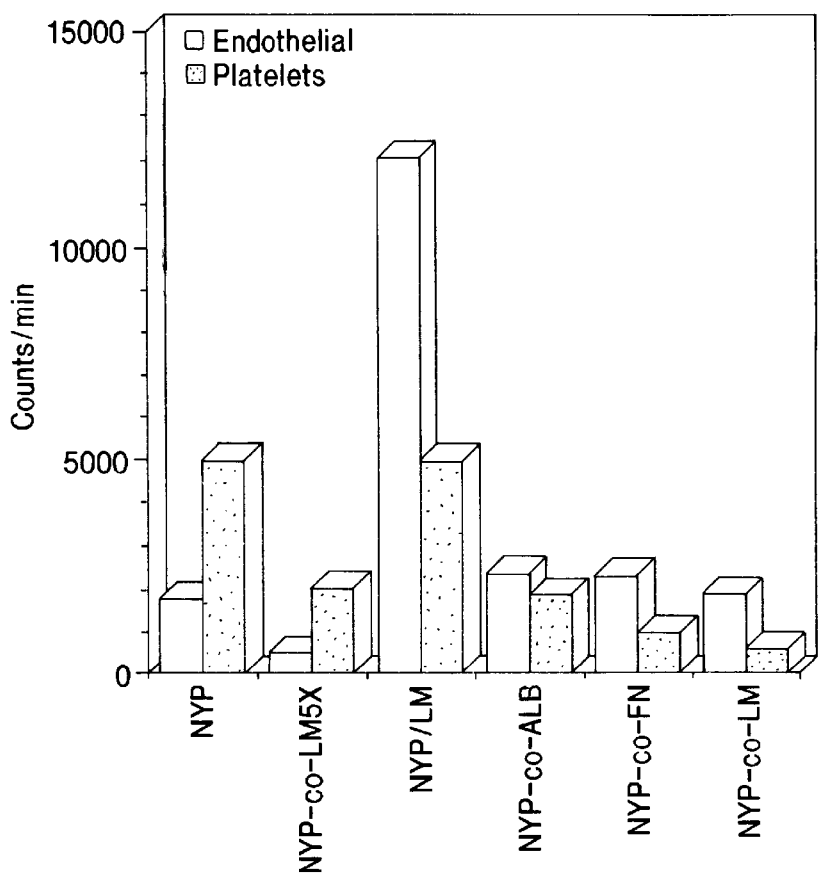
Figure 7:
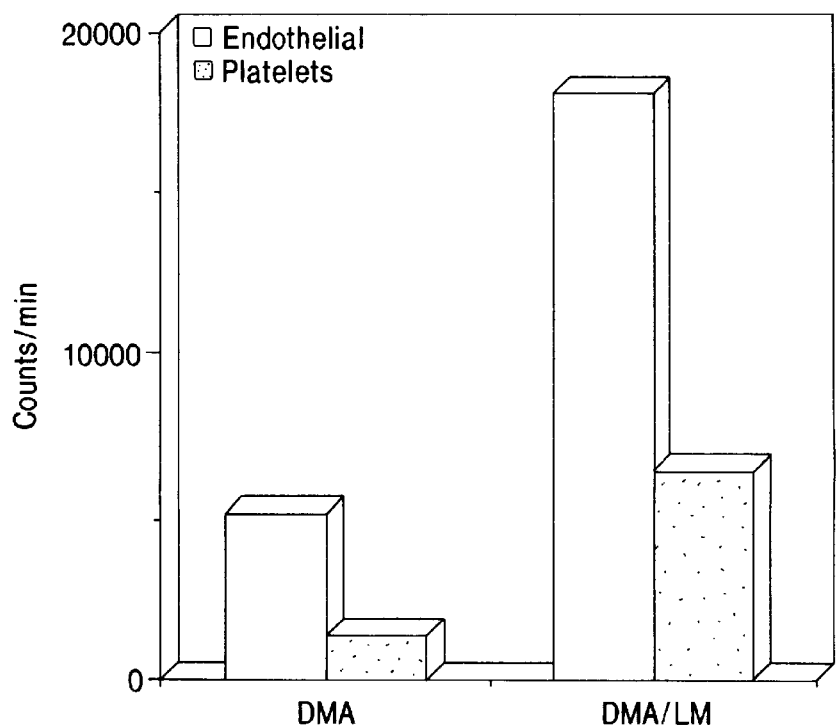
Figure 8:
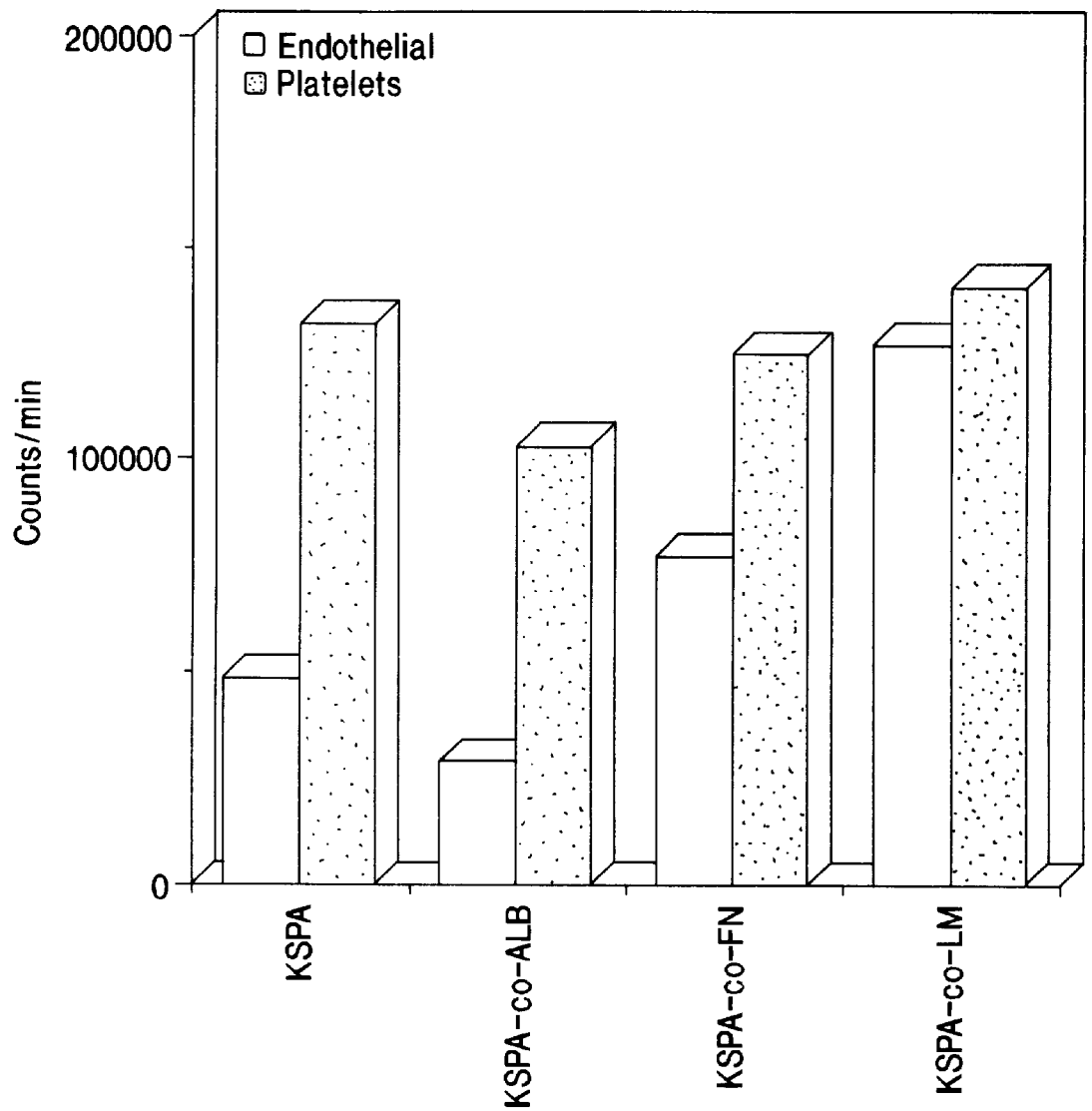

The incorporation of either laminin or fibronectin into the grafts produces a much stronger affinity for endothelial cell adhesion compared to a Hydrograft™ matrix without the biofunctional molecules (FIGS. 6, 7 and 8). Dip-coated samples also show higher endothelial adhesion, but the long-term stability of dip-coated grafts may not be as good as the radiation formed complex Hydrografts™.

PVP and DMA Hydrograft™ matrices are also readily prepared with 0.1–50 wt % basement membrane and serum proteins (albumin, collagen, laminin, fibronectin) on PUR, silicone and fluorocarbon polymer substrates. Using the plasma/gamma process, metal endoluminal stent materials (stainless steel and tantalum) were also readily surface modified with hydrophilic polymer surfaces containing heparin, laminin, albumin and collagen and exhibited lower platelet adhesion (non-thrombogenic properties) in vitro and using A-V shunt tests in canines.

EXAMPLE 3

Gamma Induced Grafting of PVP Hydrografts™ Containing Carboxymethylcellulose (CMC) or Hyaluronic Acid (HA) on PMMA Viscoelastic water-soluble polymers such as carboxymethylcellulose (CMC) and hyaluronic acid (HA) have been widely used to minimize contact adhesion between fragile tissues and instrument or device surfaces, i.e., IOLs and the corneal endothelium during cataract surgery. A permanent graft of such substances within a stable matrix is sought to provide long-term protection of delicate vascular, serosal, mucosal and ocular tissues. HA and CMC modified surfaces also exhibit useful properties for blood contacting devices. This example is concerned with gamma induced grafting of PVP containing CMC and HA on PMMA substrates.

Materials
PMMA slabs (12 mm×24 mm×2 mm)
HA (from Genzyme Corporation)
CMC (from Aqualon Corporation)
NVP (purified by vacuum distillation)

Methods
PMMA slabs were sonicated twice in 0.1% aqueous Triton X-100 for 30 minutes and 4 times in distilled water for 20 minutes, then vacuum dried at 60° C. Monomer pre-soaking was carried out in 40% NVP at 60° C. for 4 hours.

Step 1:
Samples were irradiated in 15% NVP to a dose of 0.01 Mrad, then rinsed with distilled water after removal from the polymer solution and vacuum dried at 60° C.

Step 2:
The NVP grafted samples were transferred to the grafting solutions, vacuum degassed and irradiated to an additional dose of 0.06 Mrad.

Results
Gravimetric Analysis And Contact Angle
Table 5 summarizes the grafting data.

TABLE 5

| | Concentration | | Graft Yield | Contact Angle |
|---|---|---|---|---|
| Sample # | % CMC | % NVP | Wt % | θ° (air) |
| 1 | 1 | 10 | 3 | 15 |
| 2 | 2 | 10 | 4 | 13 |
| 3 | 3 | 10 | 4 | 13 |
| Sample # | % HA | % NVP | Wt % | θ° (air) |
| 4 | 0.1 | 10 | 1 | 18 |
| 5 | 0.2 | 10 | 3 | 18 |
| 6 | 0.3 | 10 | 3 | 17 |
| 4* | 0 | 10 | 3 | 19 |

*Control sample (no added biofunctional molecule)

Figure 9:
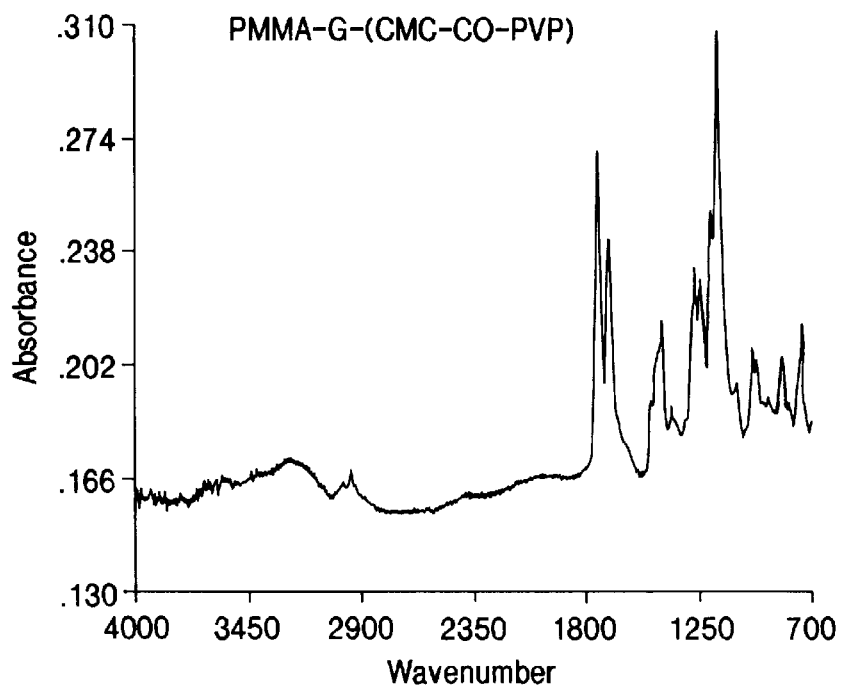
Figure 10:
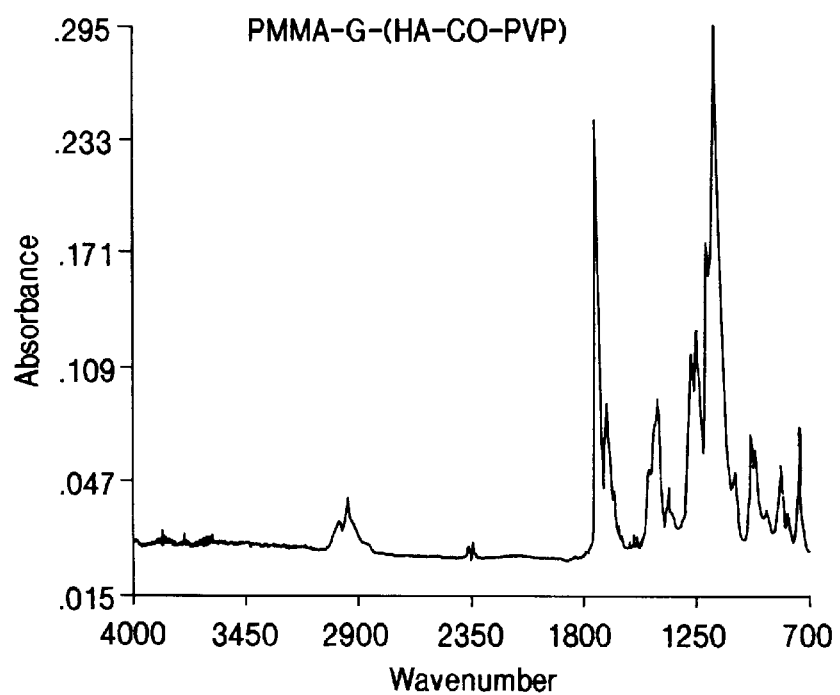

FT-IR analysis of (CMC-co-PVP)-g-PMMA and (HA-co-PVP)-g-PMMA samples (FIGS. 9 and 10) reveals an increased intensity of the absorption bands characteristic of the CMC and HA in the grafts compared to PMMA-g-PVP samples. In addition, a broad hydroxyl (OH) absorption in the region of 3300–2900 cm$^{-1}$ was also found. (HA-co-PVP)-g-PMMA samples (FIG. 10) showed an increase in the carbonyl peak at 1650 cm$^{-1}$.

Enhanced biocompatibility of surface modified PMMA IOLs by immobilized heparin or hyaluronate has been reported in the literature. However, permanent, chemically bound grafts incorporated into a radiation graft hydrophilic polymer matrix (i.e., PVP) affords more stability and long-term efficacy when compared to methods used in the prior art where the polysaccharide is simply coated as an ionic complex or immobilized on the surface via physically adsorbed polyethyleneimine. Most important, the hydrophilic polymer matrix provides a surface "water cushion" which is less adherent to fragile tissues and cells to thereby inhibit vascular or ocular tissue trauma.

Cell Adhesion

The cell adhesion tests using chick embryo and lens epithelial cell cultures showed a major reduction in cell adhesion and spreading on Hydrograft™ and Hydrograft™/biofunctional molecule surfaces using hydrophobic substrates such as PMMA, silicone, polypropylene, polycarbonate, and FEP or PTFE fluorocarbon polymers. (HA-co-PVP)-g-PMMA and (CMC-co-PVP)-g-PMMA surfaces, for example, support no cell adhesion and sample surfaces were perfectly clean after 8 hours cell incubation.

EXAMPLE 4

This example illustrates the novel incorporation of a major serum protein (albumin), a natural anionic tissue polysaccharide (chondroitin sulfate), an antibiotic drug (gentamicin), anti-inflammatory drugs (ibuprofen and endomethacin), anti-tumor drugs (Novantronem and ARA-C) and a major basement membrane protein (collagen IV) into hydrophilic radiation graft surfaces using PMMA as a model substrate and NVP as a model hydrophilic monomer.

The PMMA for this example was in the form of 1 cm×3 cm×0.1 cm thick or 1 cm×1 cm×0.1 cm thick pieces. The N-vinylpyrrolidone was distilled under nitrogen and stored at 4° C. until use. Dilutions were made just prior to pre-soaking and grafting.

Biofunctional Molecules

Albumin (bovine) was stored at 4° C. until use. Albumin solutions (3–30%) were prepared in distilled water and mixed or diluted with monomer solution as required.

Collagen IV (Sigma) was stored at 4° C. until use. Solutions (3–10 wt %) were prepared in distilled water just prior to mixing with monomers for graft polymerization.

Chondroitin sulfate was refrigerated at 4° C. and solutions were prepared prior to polymerizations (3–10 wt %).

Ibuprofen was stored at 4° C. until use and solutions of 3 wt % in 0.3N NaOH were prepared for graft polymerizations.

Gentamicin sulfate was stored at 4° C. until use. Solution concentrations in distilled water were 3–30%.

Endomethacin, Novantrone™ and ARA-C were stored and dissolved in distilled water to concentrations in the range of 1–30% as required.

PMMA substrate samples were sonicated in 60° C. Triton-X solution (0.1%) for 10 minutes, washed individually in warm water, sonicated in hot water for 10 minutes and rinsed 3 times in deionized water for 10 minutes. The substrates were dried in vacuum and stored in a desiccator.

Radiation Graft Polymerization of NVP with Albumin

One-Step Graft

1. Pre-soak PMMA samples in 40% NVP at 60° C. for 4 hours.
2. Transfer PMMA -samples to 10% NVP-3% albumin, degas, irradiate to 0.15 Mrad (at 701 rads/min.) 3. Rinse in hot water. Repeatedly rinse with distilled water at room temperature until the wash water shows no significant absorbance (at 195 nm due to PVP and at 233 cm due to NVP) in the UV/VIS.

Two-Step Graft

1. Pre-soak PMMA samples in 40% NVP at 60° C. for 4 hours.
2. Transfer to 10% NVP, 3% albumin, degas and irradiate to 0.06 Mrad.
3. Rinse in hot water. Repeatedly rinse with distilled water at room temperature until the wash water shows no significant absorbance in the UV/VIS.

Three-Step Graft

1. Pre-soak PMMA samples in 40% NVP at 60° C. for 4 hours.
2. Transfer PMMA to 10% NVP, degas and irradiate to 0.10 Mrad.
3. Wash in water at 60° C.
4. Dry under vacuum at 60° C.
5. Soak for 24 hours in a 300 mg/ml solution of bovine serum albumin.
6. Dry under vacuum at room temperature.
7. Transfer to 10% NVP, 3% albumin, degas and irradiate to 0.05 Mrad.
8. Wash in water as above.

Radiation Graft Polymerization of NVP with Chondroitin Sulfate

One-Step Graft

The procedure was the same as above with albumin, except that the polymerizing solution was 10% NVP, 3% chondroitin sulfate.

Two-Step Graft

The procedure was the same as above with albumin, except that the second grafting solution was 10% NVP, 3% chondroitin sulfate.

Three-Step Graft

The procedure was the same as above with albumin, except that the concentration of the soaking solution was 30 mg/ml chondroitin sulfate and the second grafting solution was 10% NVP, 3% chondroitin sulfate.

Radiation Graft Polymerization of NVP with Gentamicin Sulfate

One-Step Graft

The procedure was the same as above, except that the polymerizing solution was 10% NVP, 3% gentamicin sulfate.

Two-Step Graft

The procedure was the same as above, except that the second grafting solution was 10% NVP, 3% gentamicin sulfate.

Three-Step Graft

The procedure was the same as above, except that the concentration of the soaking solution was 300 mg/ml gentamicin sulfate and the second grafting solution was 10% NVP, 3% gentamicin sulfate.

Radiation Graft Polymerization of Ibuprofen

One-Step Graft

The procedure was the same as above, except that the polymerizing solution was 10% NVP, 3% ibuprofen in 0.3N NaOH.

Two-Step Graft

The procedure was the same as above, except that the second grafting solution was 10% NVP, 3% ibuprofen in 0.3N NaOH.

Three-Step Graft

The procedure was the same as above, except that the concentration of the soaking solution was 300 mg/ml ibuprofen in 0.3N NaOH and the second grafting solution was 10% NVP, 3% ibuprofen in 0.3N NaOH.

Characterization of PVP/Albumin-g-PMMA

Gravimetric analyses data for PVP/ALB-g-PMMA are shown in Table 6. The albumin graft samples polymerized in two- and three-step procedures had a higher percent graft than for the one-step procedure which is comparable to the graft efficiency with only NVP monomer.

TABLE 6

Gravimetric Analysis For PVP/ALB-g-PMMA

| Process | PVP/ALB-g-PMMA % Graft | PVP-g-PMMA % Graft |
|---|---|---|
| One-Step | 4.3 | 3.7 |
| Two-Step | 6.6 | 6.7 |
| Three-Step | 7.5 | 7.2 |

Captive air bubble contact angle measurements for PVP/ALB-g-PMMA were 16–18° indicating the very hydrophilic surfaces produced as compared to ungrafted PMMA (ca. 70°).

The PVP/ALB-g-PMMA grafts exhibit visible regions by optical microscopy near the surface corresponding to the grafts.

TABLE 7

Graft Thickness For PVP/ALB-g-PMMA

| | PVP/ALB-g-PMMA | | PVP-g-PMMA | |
|---|---|---|---|---|
| Process | measured ($\mu$m) | calculated* ($\mu$m) | measured ($\mu$m) | calculated* ($\mu$m) |
| One-Step | 100 | 63 | 101 | 50 |
| Two-Step | 125 | 90 | 128 | 93 |
| Three-Step | 113 | 100 | 114 | 92 |

*From gravimetric analyses

Graft thicknesses calculated from gravimetric analysis and optically measured for the three procedures correlated reasonably well (Table 7). Differences of 20–30% may be attributed to the assumption that all samples have identical surface areas.

FT-IR/ATR was performed on PVP/ALB-g-PMMA.

The expanded region of the PVP-g-PMMA shows two peaks, one at 1726 cm$^{-1}$ (a) and a second at 1662 cm$^{-1}$ (b). They are the PMMA ester and PVP amide carbonyls, respectively.

Albumin containing grafts show peaks at 1652 cm$^{-1}$ (b), the amide carbonyl assigned to albumin, and a peak at 1543 cm$^{-1}$ (c), an N-H bending peak also assigned to albumin.

ESCA/XPS spectra (Table 8) indicate an elevated O/C ratio for PVP/ALB-g-PMMA of ca. 30% compared to PVP-g-PMMA without albumin.

TABLE 8

ESCA Data For PVP/ALB-g-PMMA

| | % Atomic Concentration | | | |
|---|---|---|---|---|
| Sample | C1s | O1s | N1s | O/C |
| PVP | 72 | 12.5 | 12.5 | 0.17 |
| PVP/ALB | 78 | 17.0 | 5.0 | 0.22 |

Lens Epithelial Cell Adhesion Tests

For various medical device applications, surfaces that do not promote the adhesion and spreading of cells such as platelets or lens epithelial cells are desirable. A summary of results obtained for three-step PVP/ALB-g-PMMA is shown in Table 9.

Previous studies have shown that PVP-g-PMMA compared with PMMA reduces the adhesion of lens epithelial cells. The inclusion of albumin into grafts appears to further improve the non-adherent surface properties of the PVP-g-PMMA.

TABLE 9

Lens Epithelial Cell Adhesion Test Results For PVP/ALB-g-PMMA And Controls

| Sample | Result |
|---|---|
| PVP/ALB-g-PMMA | Virtually no cells |
| PVP-g-PMMA | Few to moderate # of cells |
| PMMA | Large # of cells, with spreading |

Vascular Endothelial and Platelet Adhesion

For vascular applications, an ideal surface would promote vascular endothelial cell adhesion and inhibit platelet adhesion. Vascular endothelial cell and platelet adhesion in vitro tests were performed on the two-step PVP/ALB-g-PMMA graft and compared to PVP-g-PMMA and the PMMA substrate (Table 10).

TABLE 10

Vascular Endothelial Cell And Platelet Adhesion Test Results For PVP/ALB-g-PMMA

| Sample | Endothelial Cell Count | Normalized Count* |
|---|---|---|
| PMMA | 26977 | 1.0 |
| PVP | 1201 | 0.03 |
| PVP/ALB | 2398 | 0.07 |

| Sample | Platelet Count | Normalized Count |
|---|---|---|
| PMMA | 65434 | 1.0 |
| PVP | 9115 | 0.20 |
| PVP/ALB | 1908 | 0.03 |

*Cell counts normalized to PMMA to compare results.

PVP/ALB-g-PMMA compared with PVP-g-PMMA showed a significant improvement, i.e., less platelet adhesion as well as greater endothelial cell adhesion. It has been reported that albuminated surfaces improve non-thrombogenic properties by preventing platelet and cell adhesion. The reduction in platelet adhesion to PVP/ALB-g-PMMA may, therefore, be attributed to the albumin in the Hydrograft™.

Albumin Concentration in Graft

The 10% NVP/3% albumin solution grafted homogeneously and contained 21% albumin in all cases. PVP/ALB in the grafting solution and in the wash water were analyzed indicating that essentially all albumin stays in the graft. For the three-step procedure, the majority of the incorporated albumin came from the grafting, as opposed to the soaking.

FT-IR/ATR analysis showed a shift in the carbonyl peak indicating the presence of albumin in the PVP/ALB grafts.

The O/C ratios by XPS analyses for PVP/ALB-g-PMMA compared with PVP-g-PMMA also afforded evidence for the albumin incorporation in the graft. The addition of albumin enhanced the non-adherent surface properties of the PVP-g-PMMA in lens epithelial adhesion and spreading tests and a significant reduction in platelet adhesion for PVP/ALB-g-PMMA versus PVP-g-PMMA was observed for in vitro vascular endothelial adhesion tests due to the albumin in the grafts.

Surface Grafting Of NVP-Chondroitin Sulfate (CS) on PMMA Gravimetric analyses performed on PVP/CS-g-PMMA are summarized in Table 11. The percent graft for PVP/CS-g-PMMA followed the same trend as previously discussed for PVP/ALB-g-PMMA. The percent graft was higher for the two- and three-step procedures.

TABLE 11

Gravimetric Analysis For PVP/CS-g-PMMA

| Process | PVP/CS-g-PMMA % Graft | PVP-g-PMMA % Graft |
|---|---|---|
| One-Step | 3.8 | 3.7 |
| Two-Step | 7.0 | 6.7 |
| Three-Step | 7.5 | 7.2 |

Contact Angle

Contact angles for PVP/CS-g-PMMA grafts were in the range of 18–28° indicating their hydrophilicity. PVP/CS-tg-PMMA Graft Thickness The difference in graft thicknesses (Table 12) for PVP/CS-g-PMMA compositions correlates with the gravimetric estimates of percent graft. Differences in graft thicknesses calculated from gravimetric analysis and optical measurements are small except for the one-step procedure. As with PVP/ALB-g-PMMA, differences between the graft thickness for PVP/CS-g-PMMA and PVP-g-PMMA are negligible and suggest that PVP/CS compositions graft efficiently.

TABLE 12

Graft Thickness For PVP/CS-g-PMMA

| | PVP/CS-g-PMMA | | PVP-g-PMMA | |
|---|---|---|---|---|
| Process | measured ($\mu$m) | calculated* ($\mu$m) | measured ($\mu$m) | calculated* ($\mu$m) |
| One-Step | 94 | 60 | 101 | 50 |
| Two-Step | 128 | 100 | 128 | 93 |
| Three-Step | 115 | 100 | 114 | 92 |

*From gravimetric analyses

FT-IR/ATR spectra for a three-step PVP/CS-g-PMMA has peaks at 1726 cm$^{-1}$ (a) and 1685 cm$^{-1}$ (b) and a shoulder at 1664 cm$^{-1}$ (c). The PMMA ester carbonyl is at 1726 cm$^{-1}$ (a), but the peak at 1685 cm$^{-1}$ (b) is due to the chondroitin sulfate in the Hydrograft™.

Analysis of PVP/CS-g-PMMA by ESCA/XPS showed a 30% increase in the O/C ratio when compared with PVP-g-PMMA, indicative of the presence of CS in the graft.

Based on the concentration of CS in the monomer solution and the amount analyzed in the wash, the loading of chondroitin sulfate in the graft was ca. 7%.

Radiation Graft Polymerization Using Gentamicin Sulfate (GS)—NVP

Gravimetric analyses for the gentamicin sulfate samples are summarized in Table 13.

TABLE 13

Gravimetric Analysis For PVP/GS-g-PMMA

| Process | PVP/GS-g-PMMA % Graft | PVP-g-PMMA % Graft |
|---|---|---|
| One-Step | 3.0 | 3.7 |
| Two-Step | 6.9 | 6.7 |
| Three-Step | 6.7 | 7.2 |

Grafting was efficient by all methods and contact angles were in the range of 27–31° indicative of the hydrophilicity of the grafts.

The graft thickness in the one-step procedure is slightly lower correlating with the lower gravimetric estimate of percent graft (Table 14). Graft thickness calculated from gravimetric analysis and optical measurements for PVP/GS-g-PMMA and PVP-g-PMMA are similar, indicating that the inclusion of gentamicin sulfate does not inhibit graft polymerization efficiency.

TABLE 14

Graft Thickness For PVP/GS-g-PMMA

| | PVP/GS-g-PMMA | | PVP-g-PMMA | |
|---|---|---|---|---|
| Process | measured ($\mu$m) | calculated* ($\mu$m) | measured ($\mu$m) | calculated* ($\mu$m) |
| One-Step | 92 | 60 | 101 | 50 |
| Two-Step | 123 | 100 | 128 | 93 |
| Three-Step | 113 | 100 | 114 | 92 |

*From gravimetric analyses

FT-IR/ATR analysis for PVP/GS-g-PMMA exhibited an absorption shoulder at 1662 cm$^{-1}$ (d) which is characteristic of the shifted carbonyl from gentamicin sulfate.

ESCA/XPS data and spectra show that the shoulder on the PVP/GS-g-PMMA Cls peak is shifted to a higher binding energy. Gentamicin sulfate has two carbons that are doubly bonded to oxygen and five that are singly bonded to oxygen, while PVP has only one carbon singly bonded to oxygen. The two doubly bonded carbons in gentamicin would cause the shoulder to shift to a higher energy. Analysis of the O/C ratio for PVP/GS-g-PMMA PVP shows an increase of 15% in the oxygen content when compared with PVP-g-PMMA, further indicating the presence of GS in the graft.

Zone of inhibition test results and surface bacterial growth tests for PVP/GS-g-PMMA indicated inhibition of bacterial growth in P. aeruginosa. PMMA and PVP-g-PMMA controls showed no zones of inhibition in P. aeruginosa. PVP/GS-g-PMMA polymerized in one-, two- and three-step procedures significantly reduced surface bacterial growth for P. aeruginosa when compared with the PVP-g-PMMA and the unmodified PMMA. Both PMMA and PVP-g-PMMA supported bacterial growth. PVP-g-PMMA had the largest number of colonies and bacteria count, whereas PVP/GS-g-PMMA had minimal bacterial growth indicative of the retained bioactivity of the gentamicin in the graft surface.

PVP/GS-g-PMMA also has the advantages associated with the hydrophilic graft surface, namely, the inhibition of contact tissue damage. The incorporation of gentamicin sulfate into a hydrophilic graft surface thus offers the unique advantages of combined bacteriostatic properties and hydrophilicity.

GS uptake measured by GS solution concentration depletion for three-step PVP/GS-g-PMMA was substantial. After absorption of GMC by the Hydrograft™, water washes showed little GMC release, indicating that the major amount of gentamicin sulfate is bound into the graft.

Based on GS concentration in the graft polymerization solution and amount of GS in the water wash, the GS concentration in the graft was approximately 7% for the one-step and two-step procedures. However, in the three-step procedure, the estimated loading was 25%. The difference in these loadings arises from the large drug uptake in the three-step absorption procedure.

Radiation Graft Polymerization Using Ibuprofen (IB)—NVP

Gravimetric analyses for PVP/IB-g-PMMA are summarized in Table 15.

TABLE 15

Gravimetric Analysis For PVP/IB-g-PMMA

| Process | PVP/IB-g-PMMA % Graft | PVP-g-PMMA % Graft |
|---|---|---|
| One-Step | 4.5 | 3.7 |
| Two-Step | 7.2 | 6.7 |
| Three-Step | 6.8 | 7.2 |

The grafting efficiency for PVP/IB-g-PMMA followed the same trend as for PVP/GS-g-PMMA with percent grafts for the two- and three-step PVP/IB-g-PMMA larger than the one-step.

Contact angles for PVP/IB-g-PMMA were in the range of 22–31° indicating hydrophilicity.

Graft thickness measurements are presented in Table 16. Differences between thickness measured optically and those calculated from gravimetric analysis are within experimental error.

TABLE 16

Graft Thickness For PVP/IB-g-PMMA

| | PVP/IB-g-PMMA | | PVP-g-PMMA | |
|---|---|---|---|---|
| Process | measured ($\mu$m) | calculated* ($\mu$m) | measured ($\mu$m) | calculated* ($\mu$m) |
| One-Step | 83 | 60 | 101 | 50 |
| Two-Step | 125 | 100 | 128 | 93 |
| Three-Step | 115 | 97 | 114 | 92 |

*From gravimetric analyses

Analyses for PVP and IB in the wash water indicated that approximately 50% of the ibuprofen was retained in the graft. The estimated loading for the one- and two-step procedures was, therefore, approximately 12% and slightly lower (8%) in the three-step method. The lower water solubility of ibuprofen probably inhibits the uptake in the three-step procedure.

The IB retains its bioactivity in the graft and also inhibits bacterial growth as shown by zone of inhibition tests for one- and two-step PVP/IB-g-PMMA using *P. aeruginosa*.

EXAPMLE 5

Basement Membrane Protein and Phospholipid Mixed Grafts on Vascular Prostheses and Stents A complex mixture of 60% laminin, 30% Type IV collagen and 10% heparin in aqueous NVP monomer solution (12% NVP and 3% protein/polysaccharide mix) is used in the two-step graft procedure (initial PVP/pre-soak graft at 0.1 Mrad followed by biofunctional molecule mixture with monomer grafted at 0.05 Mrad) to yield a surface modification composition on PMMA which approximates the ratio of these biofunctional compounds in arterial basement membrane. The same procedure is used for grafts on PUR and PDMSO. All surfaces are highly hydrophilic (20° contact angle by underwater air bubble) and exhibit the following properties: low platelet adhesion (in vitro human platelet test and canine A-V shunt in vivo test with indium''' label), improved endothelial cell adhesion (compared to PVP graft), and low thrombogenicity in canine A-V shunt test. This surface graft, therefore, exhibits improved properties for various blood contact device applications such as vascular prostheses (especially for small diameters, i.e., <4–5 mm), stents used following angioplasty, and heart valve or ventricular assist devices, and the like.

As another embodiment of this example, stainless steel and tantalum endoluminal stents are modified with the basement membrane biomolecular mixture noted above in DMA, and in KSPA polymer graft matrices. Both metal surfaces are treated by the plasma/gamma process in which (a) they are subjected to an initial RF plasma surface activation followed by (b) a one-step gamma graft polymerization carried to 0.1 Mrad. The biofunctional surface modifications with both DMA and the anionic KSPA matrices are less thrombogenic than the metals and exhibit improved blood compatibility tested in canine A-V blood shunt test (with much lower platelet adhesion than the metal surfaces). Such biofunctional surface modified stents are especially valuable for improved post-angioplasty stenting devices and exhibit improved long-term vessel patency.

In another series of experiments, hydrophilic polymer grafts on PMMA and silicone substrates, containing (a) the heparin/laminin/collagen IV mix with 12-PL and with HEMA-PL phospholipids (1%) are readily prepared with 0.05 Mrad final graft radiation dose yielding more biomimetic surface properties and improved non-thrombogenic properties.

EXAMPLE 6

Silicone Mammary Implant with Improved Surface Properties

Silicone envelopes of mammary implants are modified by the two-step process (with NVP pre-soak) and radiation surface graft modified with DMA and with KSPA graft matrices containing a heparin-mannitol-prednisone mix (3% total in the ratio 1:3:1) with 10% of the hydrophilic monomer. The pre-soak graft condition is 0.1 Mrad and the biofunctional mix/monomer graft is at 0.05 Mrad. The resulting silicone surface is significantly improved in many ways: (a) exhibits less tissue adhesion and trauma during surgical implantation, (b) is less adherent for inflammatory cells to reduce post-operative inflammation, (c) is less adherent for pathogens to inhibit infectious complications, (d) is less permeable to silicone fluids contained within the silicone gel in the implants due to the surface hydrophilicity, and most important (e) exhibits minimal hard fibrous capsule formation which normally surrounds such implants due to surface inflammatory and foreign body reactions. Concerning this latter point, a major problem with such devices, the biofunctional graft acts to inhibit inflammatory reactions due to the localized corticosteroid activity of the prednisone, the anti-oxidant/anti-inflammatory function of the mannitol, and the fibroblast/smooth muscle cell inhibition and blotting cascade inhibition function of the heparin. Rabbit implants using miniature (2–4 g) silicone/silicone gel implants examined at periods of 2 weeks to 6 months confirm the more favorable behavior (reduced incidence of thick contractile capsule) as compared with unmodified or simply Hydrograft™ modified implants.

EXAMPLE 7

PMMA and Silicone Ocular Implants with Improved Properties Using Biofunctional Hydrophilic Polymer Surface Modification One-piece PMMA intraocular lens (IOL) implants with 6 mm diameter optics and 13 mm overall diameter are modified by using the two-step (pre-soak) process with NVP pre-soak and 0.1 Mrad grafting followed by 0.05 Mrad grafting in an aqueous monomer-biofunctional molecule solution containing 10% monomer plus 5% of a 1:2:1 ratio of heparin/HEMA-PL/prednisone mix. The resulting surface modified IOLs exhibit very low inflammatory cell adhesion post-operatively in a rabbit anterior chamber implant model even using 100 mg of injected autologous rabbit lens cortex to induce an acute inflammatory reaction. Similarly, improved results are observed for silicone IOLs surface modified using the above biofunctional molecule-monomer mixture.

Another surface modification composition applied as above by the two-step process but using a 10% NVP monomer mix with 1% of the cytotoxic drug, ARA-C, yields a tissue protective hydrophilic graft (25° contact angle) which also exhibits (in posterior chamber rabbit implant tests) mild but prolonged inhibition of post-operative epithelial cell proliferation, thereby significantly reducing the incidence of posterior capsule opacification (secondary cataract). With methotrexate added as above as the cytotoxic drug, a comparable reduction in this significant ocular surgery complication is observed.

EXAMPLE 8

Vascular and Urinary Tract Catheters Surface Modified with Biofunctional Hydrophilic Polymer Grafts Nylon vascular catheters are surface modified with a 12% aqueous KSPA monomer solution containing 2% heparin and gentamicin in a 1:1 ratio. A two-step process is used with NVP at 0.1 Mrad in the first step and the above KSPA/heparin/gentamicin mix in the second step. The resulting highly hydrophilic catheter surfaces greatly reduce vascular endothelium damage during insertion and removal, are much easier (lower friction) to insert and remove, exhibit very low thrombogenicity and have anti-bacterial properties to minimize the risk of infectious complications, as compared to conventional nylon catheters. Similar biofunctional hydrophilic surface modifications are readily prepared on polyurethane, fluorocarbon, polyvinyl chloride and silicone catheter (and balloon) surfaces with similar major improvements in clinically important properties.

As above, using KSPA and DMA monomers, Foley urinary tract balloon catheters (silicone and PUR) as well as ureteral stents are modified to yield devices which inhibit infectious complications due to the gentamicin anti-bacterial properties and reduce the incidence of catheter and stent deposits which makes removal painful and damaging to the fragile mucosal tissues.

We claim:

1. A method for modifying the surface of a material adapted for contact with tissue of a human or non-human animal to impart biofunctional, bioactive or biomimetic properties to said surface comprising:
    (a) exposing said surface to a solution comprising (1) a neutral or ionic water-soluble, hydrophilic, vinylic monomer, salt or mixture thereof, and (2) at least one biofunctional agent, the concentration of said biofunctional agent in said solution being in the range of from about 0.001% to about 50%, by weight; and
    (b) irradiating said surface with gamma or electron beam irradiation in the presence of said solution to thereby form on said surface a graft polymerized coating, said coating having physically entrapped therein or chemically bonded thereto molecules of said at least one biofunctional agent which imparts biofunctional properties to said surface;
    wherein said gamma or electron beam irradiation induced polymerization is conducted under the following conditions:
        (i) concentration of monomer and biofunctional molecules in the solution in the range of from about 0.1% to about 50%, by weight;
        (ii) total gamma or electron beam dose in the range of from about 0.001 to less than about 0.50 Mrad; and
        (iii) gamma dose rate in the range of from about 10 to about 2,500 rads/min., or electron beam dose rate in the range of from about 10 to about $10^8$ rads/min.; and
    wherein the biological properties of said biofunctional agent are substantially retained under said gamma or electron beam irradiation polymerization conditions.

2. The method according to claim 1 further including one or more of the following conditions:
    (d) substantially excluding free oxygen from said graft polymerization solution;
    (e) maintaining the thickness of said polymer coating in the range of from about 100 Å to about 100 microns;
    (f) including a free radical scavenger in said aqueous graft polymerization solution; and
    (g) including in said aqueous graft polymerization solution a swelling solvent for said plastic surface.

3. The method according to claim 1 wherein said monomer is selected from the group consisting of N-vinylpyrrolidone, hydroxyethylmethacrylate, acrylamide, dimethyl-acrylamide, polyethylene glycol monomethacrylate, acryloylpolyethylene glycol, hydroxypropylacrylamide, methacrylic acid, sulfopropylacrylate, sulfopropylmethacrylate, styrenesulfonic acid, 2-acrylamide-2-methyl-1-propane sulfonic acid, vinylsulfonic acid, dimethylaminoethylmethacrylate, mixtures and salts thereof.

4. The method according to claim 1 wherein said monomer-biofunctional molecule solution contains up to about 50 wt. %, based on the total monomer weight, of an ionic monomer, a salt or mixture thereof.

5. The method according to claim 1 further including, prior to said step of polymerization, a step comprising pre-soaking said surface in at least one of said monomers or in an aqueous solution of at least one of said monomers, having a concentration of monomer therein of from about 5 to about 95%, by weight; said pre-soaking being conducted for a period of time and at a temperature sufficient to facilitate diffusion of said monomer into said surface.

6. The method according to claim 5 wherein said pre-soaking step is conducted at a temperature in the range of from about 25° C. to about 90° C. and for a period of time of from about 0.5 hour to about 48 hours.

7. The method according to claim 1 wherein said gamma or electron beam irradiation induced polymerization is conducted in multiple steps;
    the first step comprising conducting said steps (a) and (b) of claim 1 under conditions (i), (ii) and (iii) in the absence of any biofunctional agent;
    the second step comprising soaking the product of said first step in a solution of said at least one biofunctional said soaking being conducted for a period of time and at a temperature sufficient to facilitate diffusion of said at least one biofunctional agent into said polymerized surface; and
    a final step comprising conducting said steps (a) and (b) of claim 1 under conditions (i) and (iii), but wherein said total gamma or electron beam dose (i) is in the range of from about 0.001 to less than about 0.20 Mrad.

8. The method according to claim 7 further including, prior to said step of polymerization, a step comprising pre-soaking said surface in at least one of said monomers or in an aqueous solution of at least one of said monomers, having a concentration of monomer therein of from about 5 to about 95%, by weight; said pre-soaking being conducted for a period of time and at a temperature sufficient to facilitate diffusion of said monomer into said surface.

9. The method according to claim 7 wherein said pre-soaking step is conducted at a temperature in the range of from about 25° C. to about 90° C. and for a period of time of from about 0.5 hour to about 48 hours.

10. The method according to claim 8 wherein a product of said first step is soaked in an aqueous solution of said at least one biofunctional agent, and said aqueous solution may contain a water-soluble organic solvent for the biofunctional component(s).

11. The method according to claim 10 wherein the concentration of said biofunctional agent in said solution is in the range of from about 0.001% to about 10% by weight.

12. The method according to claim 7 wherein said soaking is conducted at a temperature of from about 4° to about 90° and for a period of time of from about 5 minutes to about 24 hours.

13. The method according to claim 1 wherein said graft polymerized coating is hydrophilic.

14. The method according to claim 1 wherein said material surface is metallic, polymeric, ceramic, glass or quartz.

15. The method according to claim 14 wherein said material surface is polymeric and is selected from the group consisting of polyacrylates, polymethacrylates, polyolefins, ethylene-propylene copolymers, styrene-butadiene copolymers, styrene-ethylene-butadiene copolymers, polycarbonates, fluorocarbon polymers, polysiloxanes, siloxane block copolymers, polyurethanes, polyvinylchloride, polyesters, mixtures and copolymers thereof.

16. The method according to claim 1 wherein said biofunctional agent is a beta-blocker, a steroidal or non-steroidal anti-inflammatory agent, an anti-bacterial agent, a protein, a cytotoxic or anti-tumor agent, a fibrinolytic agent, a polysaccharide, an anti-oxidant or anti-oxidant enzyme, a growth factor or growth hormone, an anti-bloodclotting agent, a phospholipid, a smooth muscle cell inhibitor, a vascular basement membrane component or an immune modulator.

17. A method according to claim 1 including the step of activating said surface prior to said gamma irradiation or electron beam induced polymerization step by exposing said surface to a glow discharge plasma (GDP) having a power and for a time sufficient to induce grafting sites on said surface which are available for said subsequent gamma irradiation or electron beam polymerization.

18. The method according to claim 17, wherein said GDP is RF-, microwave- or DC discharge-generated.

19. The method according to claim 17, wherein said surface is exposed to RF-GDP having a power in the range of from about 1 W to about 500 W or more.

20. The method according to claim 17, wherein said surface is exposed to RF-GDP for a time in the range of from about 0.1 second to about 120 minutes.

21. The method according to claim 17, wherein said GDP treated surface is exposed to air, water vapor or oxygen before said gamma irradiation induced polymerization.

22. A composition of matter comprising a coating formed on a substrate adapted for contact with tissue of a human or non-human animal by a method comprising:

(a) exposing said substrate to a solution comprising (1) an ethylenically unsaturated neutral or ionic, water-soluble, hydrophilic monomer, salt or mixture thereof capable, via said ethylenic unsaturation, of gamma irradiation or electron beam induced polymerization, and (2) at least one biofunctional agent, the concentration of said biofunctional agent in said solution being in the range of from about 0.001% to about 50%, by weight; and (b) irradiating said substrate with gamma or electron beam irradiation in the presence of said solution to thereby form on said substrate a graft polymerized coating, said coating having physically entrapped therein or chemically bonded thereto molecules of said at least one biofunctional agent which imparts biomimetic properties to said substrate;

wherein said gamma or electron beam irradiation induced polymerization is conducted under the following conditions:

(i) monomer and biofunctional molecules concentration in the solution in the range of from about 0.1% to about 50%, by weight;

(ii) total gamma or electron beam dose in the range of from about 0.001 to less than about 0.50 Mrad; and (iii) gamma dose rate in the range of from about 10 to about 2,500 rads/min., or electron beam dose rate in the range of from about 10 to about $10^8$ rads/min.; and wherein the biological properties of said biofunctional agent are substantially unaffected by said gamma or electron beam irradiation polymerization conditions.

23. The composition according to claim 22 wherein said monomer is selected from the group consisting of N-vinyl-pyrrolidone, hydroxyethylmethacrylate, acrylamide, dimethylacrylamide, polyethylene glycol monomethacrylate, acryloylpolyethylene glycol, hydroxypropylacrylamide, methacrylic acid, sulfopropylacrylate, sulfopropylmethacrylate, styrene-sulfonic acid, 2-acrylamide-2-methyl-1-propane sulfonic acid, vinylsulfonic acid, dimethylaminoethylmethacrylate, mixtures and salts thereof.

24. The composition according to claim 22 wherein said monomer-biofunctional molecule solution contains up to about 50 wt. %, based on the total monomer weight, of an ionic monomer, a salt or mixture thereof.

25. The composition according to claim 22 wherein said method further includes, prior to said step of polymerization, a step comprising pre-soaking said substrate in at least one of said monomers or in an aqueous solution of at least one of said monomers, having a concentration of monomer therein of from about 5 to about 95%, by weight; said pre-soaking being conducted for a period of time and at a temperature sufficient to facilitate diffusion of said monomer into said substrate.

26. The composition according to claim 25 wherein said pre-soaking step is conducted at a temperature in the range of from about 25° C. to about 90° C. and for a period of time of from about 0.5 hour to about 48 hours.

27. The composition according to claim 22 wherein said gamma or electron beam irradiation induced polymerization is conducted in multiple steps;

the first step comprising conducting said steps (a) and (b) of claim 22 under conditions (i), (ii) and (iii) in the absence of any biofunctional agent;

the second step comprising soaking the product of said first step in a solution of said at least one biofunctional said soaking being conducted for a period of time and at a temperature sufficient to facilitate diffusion of said at least one biofunctional agent into said polymerized substrate; and a final step comprising conducting said steps (a) and (b) of claim 22 under conditions (i) and (iii), but wherein said total gamma or electron beam dose (i) is in the range of from about 0.001 to less than about 0.20 Mrad.

28. The composition according to claim 27 further including, prior to said step of polymerization, a step comprising pre-soaking said substrate in at least one of said monomers or in an aqueous solution of at least one of said monomers, having a concentration of monomer therein of from about 5 to about 95%, by weight; said pre-soaking being conducted for a period of time and at a temperature sufficient to facilitate diffusion of said monomer into said substrate.

29. The composition according to claim 27 wherein said pre-soaking step is conducted at a temperature in the range of from about 25° C. to about 90° C. and for a period of time of from about 0.5 hour to about 48 hours.

30. The composition according to claim 22 wherein said graft polymerized coating is hydrophilic.

31. The composition according to claim 22 wherein said substrate is metallic, polymeric, ceramic, glass or quartz.

32. The composition according to claim 31 wherein said substrate is polymeric and is selected from the group consisting of, polyacrylates, polymethacrylates, polyolefins, ethylene-propylene copolymers, styrene-butadiene copolymers, styrene-ethylene-butadiene copolymers, polycarbonates, fluorocarbon polymers, polysiloxanes, siloxane block copolymers, polyurethanes, polyvinylchloride, polyesters, mixtures and copolymers thereof.

33. The composition according to claim 22 wherein said biofunctional agent is a beta-blocker, a steroidal or non-steroidal anti-inflammatory agent, an anti-bacterial agent, a protein, a cytotoxic or anti-tumor agent, a fibrinolytic agent, a polysaccharide, an anti-oxidant or anti-oxidant enzyme, a growth factor or growth hormone, an anti-bloodclotting agent, a phospholipid, a smooth muscle cell inhibitor, a vascular basement membrane component or an immune modulator.

34. A composition according to claim 22 wherein said method includes the step of activating said substrate prior to said gamma irradiation or electron beam induced polymerization step by exposing said substrate to a glow discharge plasma (GDP) having a power and for a time sufficient to induce grafting sites on said substrate which are available for said subsequent gamma irradiation or electron beam polymerization.

35. The composition according to claim 34, wherein said GDP is RF-, microwave- or DC discharge-generated.

36. The composition according to claim 34, wherein said substrate is exposed to RF-GDP having a power in the range of from about 1 W to about 500 W or more.

37. The composition according to claim 34, wherein said substrate is exposed to RF-GDP for a time in the range of from about 0.1 second to about 120 minutes.

38. The composition according to claim 34 wherein said GDP treated substrate is exposed to air, water vapor or oxygen before said gamma irradiation induced polymerization.

39. An article comprised at least in part of a material produced by a method for modifying the surface of a material adapted for contact with tissue of a human or non-human animal to impart biofunctional, bioactive or biomimetic properties to said surface comprising:

(a) exposing said surface to a solution comprising (1) a neutral or ionic water-soluble, hydrophilic, vinylic monomer, salt or mixture thereof, and (2) at least one biofunctional agent, the concentration of said biofunctional agent in said solution being in the range of from about 0.001% to about 50%, by weight; and (b) irradiating said surface with gamma or electron beam irradiation in the presence of said solution to thereby form on said surface a graft polymerized coating, said coating having physically entrapped therein or chemically bonded thereto molecules of said at least one biofunctional agent which imparts biofunctional properties to said surface;

wherein said gamma or electron beam irradiation induced polymerization is conducted under the following conditions:

(i) concentration of monomer and biofunctional molecules in the solution in the range of from about 0.1% to about 50%, by weight;

(ii) total gamma or electron beam dose in the range of from about 0.001 to less than about 0.50 Mrad; and (iii) gamma dose rate in the range of from about 10 to about 2,500 rads/min., or electron beam dose rate in the range of from about 10 to about $10^8$ rads/min.; and wherein the biological properties of said biofunctional agent are substantially retained under said gamma or electron beam irradiation polymerization conditions.

40. An article according to claim 39 wherein said article is an ocular implant material.

41. An article according to claim 39 wherein said article is a surgical instrument.

42. An article according to claim 39 wherein said article is a medical device.

43. An article according to claim 39 wherein said article is a prosthetic implant.

44. An article according to claim 39 wherein said article is a soft or hard contact lens.

45. An article according to claim 39 wherein said article is a vascular graft or stent.

46. An article according to claim 39 wherein said article is a joint replacement composite.

47. An article according to claim 39 wherein said article is a mammary implant.

48. An article according to claim 39 wherein said article is a catheter.

49. An article according to claim 39 wherein said article is a blood bag, blood oxygenator or blood tubing.

50. An article according to claim 39 wherein said article is a dialysis membrane.

51. An article according to claim 39 wherein said article is a nerve regeneration scaffold.

* * * * *